(12) United States Patent
Millar

(10) Patent No.: US 7,700,559 B2
(45) Date of Patent: Apr. 20, 2010

(54) GONADOTROPIN RELEASING HORMONE ANALOGUES CONJUGATES WITH STEROID HORMONES

(75) Inventor: Robert Peter Millar, Edinburgh (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 10/552,110

(22) PCT Filed: Apr. 5, 2004

(86) PCT No.: PCT/GB2004/001478

§ 371 (c)(1),
(2), (4) Date: Jul. 3, 2006

(87) PCT Pub. No.: WO2004/087215

PCT Pub. Date: Oct. 14, 2004

(65) Prior Publication Data

US 2006/0247177 A1    Nov. 2, 2006

(30) Foreign Application Priority Data

Apr. 4, 2003    (GB) ................................. 0307777.3

(51) Int. Cl.
A61K 38/00    (2006.01)
A61K 38/08    (2006.01)
A61K 38/09    (2006.01)
A61K 38/24    (2006.01)
C07K 7/00    (2006.01)
C07K 7/23    (2006.01)

(52) U.S. Cl. ............................... 514/15; 514/2; 514/12; 514/13; 514/14; 514/16; 530/325; 530/326; 530/327; 530/328; 530/329; 424/1.45

(58) Field of Classification Search ........................ None
See application file for complete search history.

(56) References Cited

U.S. PATENT DOCUMENTS

| | | | |
|---|---|---|---|
| 3,813,382 A | 5/1974 | McKinley et al. |
| 3,843,065 A | 10/1974 | Horstman et al. |
| 3,849,389 A | 11/1974 | Shields |
| 3,855,199 A | 12/1974 | Foell et al. |
| 3,886,135 A | 5/1975 | McKinley et al. |
| 3,890,437 A | 6/1975 | Foell et al. |
| 3,892,723 A | 7/1975 | McKinley et al. |
| 3,896,104 A | 7/1975 | McKinley et al. |
| 3,901,872 A | 8/1975 | McKinley et al. |
| 3,914,412 A | 10/1975 | Gendrich et al. |
| 3,915,947 A | 10/1975 | Shields |
| 3,929,759 A | 12/1975 | Foell |
| 3,937,695 A | 2/1976 | Sarantakis |
| 3,953,416 A | 4/1976 | Folkers et al. |
| 3,974,135 A | 8/1976 | Folkers et al. |
| 4,010,125 A | 3/1977 | Schally et al. |
| 4,018,914 A | 4/1977 | Johnson |
| 4,022,759 A | 5/1977 | Tinney et al. |
| 4,022,760 A | 5/1977 | Tinney |
| 4,022,761 A | 5/1977 | Tinney et al. |
| 4,024,248 A | 5/1977 | Konig et al. |

(Continued)

FOREIGN PATENT DOCUMENTS

| | | |
|---|---|---|
| EP | 0 081 877 A1 | 6/1983 |
| EP | 0 192 492 A2 | 8/1986 |
| EP | 1 424 080 A | 6/2004 |
| GB | 2 310 660 A | 9/1997 |
| WO | WO 90/09799 A | 9/1990 |
| WO | WO 91/14704 | 10/1991 |
| WO | WO 93/03058 | 2/1993 |

(Continued)

OTHER PUBLICATIONS

Doyle & Egan, "Glucagon-like peptide-1." Recent Prog Horm Res., 2001, 56, 377-99.*

(Continued)

*Primary Examiner*—Anish Gupta
*Assistant Examiner*—Julie Ha
(74) *Attorney, Agent, or Firm*—Nixon Peabody LLP

(57) ABSTRACT

A compound comprising a gonadotrophin releasing hormone analogue conjugated to a hormone moiety, or a derivative thereof, which is able to bind to a plasma hormone binding protein. The compounds may be used to treat hormone-dependent disorders such as cancer, or as a contraceptive.

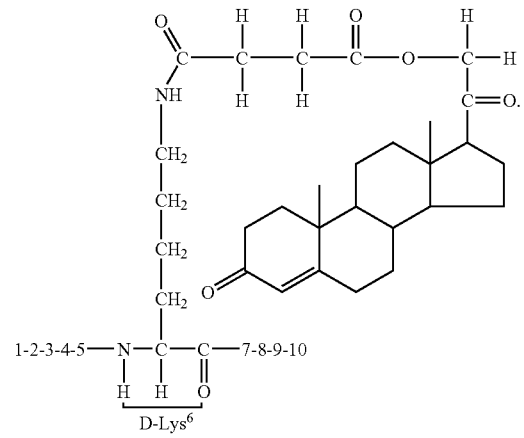

52 Claims, 8 Drawing Sheets

U.S. PATENT DOCUMENTS

| | | | |
|---|---|---|---|
| 4,034,082 | A | 7/1977 | Johnson et al. |
| 4,072,668 | A | 2/1978 | Amoss et al. |
| 4,075,189 | A | 2/1978 | Tinney |
| 4,075,192 | A | 2/1978 | Nicolaides |
| 4,086,219 | A | 4/1978 | Wittle et al. |
| 4,101,538 | A | 7/1978 | Campbell |
| 4,124,577 | A | 11/1978 | Tinney et al. |
| 4,124,578 | A | 11/1978 | Lapidus |
| 4,143,133 | A | 3/1979 | Foell et al. |
| 4,234,571 | A | 11/1980 | Nestor et al. |
| 4,253,997 | A | 3/1981 | Sarantakis |
| 4,292,313 | A | 9/1981 | Vale, Jr. et al. |
| 4,341,767 | A | 7/1982 | Nestor et al. |
| 4,504,414 | A | 3/1985 | Folkers et al. |
| 4,677,193 | A | 6/1987 | Rivier et al. |
| 4,705,778 | A | 11/1987 | Almquist et al. |
| 5,064,939 | A | 11/1991 | Rivier et al. |
| 5,371,070 | A | 12/1994 | Koerber et al. |
| 5,413,990 | A | 5/1995 | Haviv et al. |
| 5,502,035 | A | 3/1996 | Haviv et al. |
| 5,633,248 | A | 5/1997 | Kato et al. |
| 5,756,497 | A | 5/1998 | Bell et al. |
| 6,156,731 | A | 12/2000 | Grass et al. |
| 6,191,115 | B1 | 2/2001 | Haviv et al. |
| 6,211,224 | B1 * | 4/2001 | Chu et al. ............... 514/415 |

FOREIGN PATENT DOCUMENTS

| | | |
|---|---|---|
| WO | WO 94/28015 | 12/1994 |
| WO | WO 95/04541 | 2/1995 |
| WO | WO 95/28405 | 10/1995 |
| WO | WO 96/24597 | 8/1996 |
| WO | WO 97/41126 | 11/1997 |
| WO | WO 97/44041 | 11/1997 |
| WO | WO 97/44321 | 11/1997 |
| WO | WO 97/44339 | 11/1997 |
| WO | WO 98/03632 | 1/1998 |
| WO | WO 98/55505 | 12/1998 |
| WO | WO 99/21557 | 5/1999 |
| WO | WO 99/33831 | 7/1999 |
| WO | WO 99/41251 | 8/1999 |
| WO | WO 99/41252 | 8/1999 |
| WO | WO 99/46283 | 9/1999 |
| WO | WO 00/00493 | 1/2000 |
| WO | WO 00/53178 | 9/2000 |
| WO | WO 00/56739 | 9/2000 |
| WO | WO 01/78780 A1 | 10/2001 |
| WO | WO 02/02533 A1 | 10/2002 |
| WO | WO 03/015820 A1 | 2/2003 |
| WO | WO 2004/058269 A | 7/2004 |

OTHER PUBLICATIONS

Evers et al., "Somatostatin and analogues in the treatment of cancer. A review." Ann Surg., 1991, 213, 190-8.*

Definition of moiety from www.dictionary.com, pp. 1-2. Accessed Jan. 21, 2009.*

Introduction to Cancer from Merck manual, p. 1. Accessed Mar. 5, 2008.*

Clinical Aspects of Cancer from Merck manual, pp. 1-4. Accessed Mar. 5, 2008.*

Auerbach R, Akhtar N, Lewis RL, Shinners BL, "Angiogenesis assays: Problems and pitfalls", Cancer and Metastasis Reviews, 2000, 19: 167-172.*

Gura T, "Systems for Identifying New Drugs Are Often Faulty", Science, Nov. 7, 1997, 278: 1041-1042.*

Jain R, "Barriers to Drug Delivery in Solid Tumors", Scientific American Jul. 1994, 271(1): 58-65.*

Endometriosis from Merck manual, pp. 1-5. Accessed Feb. 4, 2009.*

Introduction to Infertiliy from Merck manual, pp. 1-2. Accessed Feb. 4, 2009.*

Abnormal Cervical Mucus for Infertility from Merck manual, p. 1. Accessed Feb. 4, 2009.*

Assisted Reproductive Techniques for Infertility from Merck manual, pp. 1-2. Accessed Feb. 4, 2009.*

Decreased Ovarian Reserve for Infertility from Merck manual, p. 1. Accessed Feb. 4, 2009.*

Ovulatory Dysfunction for Infertility from Merck manual, pp. 1-3. Accessed Feb. 4, 2009.*

Sperm disorders for Infertility from Merck manual, pp. 1-4. Accessed Feb. 4, 2009.*

Tubal dysfunction and pelvic lesions for Infertility from Merck manual, pp. 1-2. Accessed Feb. 4, 2009.*

Unexplained infertility for Infertility from Merck manual, pp. 1-2. Accessed Feb. 4, 2009.*

Alsenz et al., "Oral Absorption of Peptides Through the Cobalamin (Vitamin B12) Pathway in the Rat Intestine," *Pharmaceutical Research* 17(7):825-832 (2000).

Anderson, "Hormonal Contraception in the Male," *British Medical Bulletin* 56(3):717-728 (2000).

Arányi, "A Szteroid Hormonok Hatásainak Szerkezeti Alapjai," *Biológia* 30:145-169 (1982).

Arányi, "Dependence of Rate Constants of the Glucocorticoid Hormone-Receptor Interaction on Steroid Structure," *J. Steroid Biochem.* 17:137-141 (1982).

Burton & Westphal, "Steroid Hormone-Binding Proteins in Blood Plasma," *Metabolism* 21(3):253-276 (1972).

Christin-Maitre et al., "Effect of Gonadotrophin-Releasing Hormone (GnRH) Antagonist During the LH Surge in Normal Women and During Controlled Ovarian Hyperstimulation," *Clin. Endocrinol.* 52:721-726 (2000).

Cunningham et al., "Steroid Structural Requirements for High Affinity Binding to Human Sex Steroid Binding Protein (SBP)," *Steroids* 38(3):243-262 (1981).

Danforth et al., "Intermittent GNRH Antagonist Plus Progestin Contraception Conserving Tonic Ovarian Estrogen Secretion and Reducing Progestin Exposure," *Contraception* 41(6):623-631 (1990).

Ditkoff et al., "The Gonadotropin-Releasing Hormone Antagonist (Nal-Glu) Acutely Blocks the Luteinizing Hormone Surge but Allows for Resumption of Folliculogenesis in Normal Women," *Am. J. Obstet. Gynecol.* 165(6 Pt 1):1811-1817 (1991).

Duax & Griffin, "Molecular Structure, Receptor Binding and Activity of Sex Steroids," *Frontiers in Drug Research,* Alfred Benzon Symposium, 28:62-74 (1990).

Duax & Griffin, "Steroid Hormone Structure, Receptor Binding and Activity: Empirical Drug Design," *Structure-Based Drug Design,* P.W. Codding (ed.), pp. 1-14 (1998).

Duax & Griffin, "The Structure and Receptor Binding of Steroid Hormones," *Advances in Drug Research* 18:115-138 (1989).

Duncan et al., "A New Reagent Which May Be Used to Introduce Sulfhydryl Groups into Proteins, and Its Use in the Preparation of Conjugates for Immunoassay," *Anal. Biochem.* 132:68-73 (1983).

Dutta & Furr, "Luteinizing Hormone Releasing Hormone (LHRH) Analogues," *Annual Reports in Medicinal Chemistry*-20, Chapter 21, pp. 203-214 (1985).

Fraser et al., "Effect of Late Follicular Phase Administration of Antide on Ovulation and Inhibin Secretion in Macaques," Contraception 44(6):667-676 (1991).

Fraser et al., "Suppression of Luteal Function by a Luteinizing Hormone-Releasing Hormone Antagonist During the Early Luteal Phase in the Stumptailed Macaque Monkey and the Effects of Subsequent Administration of Human Chorionic Gonadotropin," *Endocrinology* 121(2):612-618 (1987).

Goulet, "Gonadotropin Releasing Hormone Antagonists," *Annual Reports in Medicinal Chemistry*-30, Chapter 18, pp. 169-178 (1995).

Kenigsberg & Hodgen, "Ovulation Inhibition by Administration of Weekly Gonadotropin-Releasing Hormone Antagonist," *J. Clin. Endocrinol. Metabol.* 62(4):734-738 (1986).

Klosterman et al., "Cortisol Levels, Binding and Properties of Corticosteroid-Binding Globulin in the Serum of Primates, " *Endocrinology* 118(1):424-434 (1986).

Lu et al., "Improved Synthesis of 4-Alkoxybenzyl Alcohol Resin," *J. Org. Chem.* 46:3433-3436 (1981).

Mattox et al., "A Comparison of Procedures for Attaching Steroidal Glucosiduronic Acids to Bovine Serum Albumin," *J. Steroid Biochem.* 10:167-172 (1979).

McEwan et al., "Synthesis and Biological Activity of Ribose-5'-Carbamate Derivatives of Vitamin $B_{12}$," *Bioconjugate Chem.* 10:1131-1136 (1999).

Mickelson et al., "Steroid-Protein Interactions. Human Corticosteroid Binding Globulin: Some Physicochemical Properties and Binding Specificity," *Biochemistry* 20:6211-6218 (1981).

Millar et al., "GnRH and GnRH Analogues: Structure, Actions and Clinical Applications," *Hormone Frontier in Gynecology* 5(4):77-83 (1998).

Millar et al., "Progress Towards the Development of Non-Peptide Orally-Active Gonadotropin-Releasing Hormone (GnRH) Antagonists: Therapeutic Implications," *British Medical Bulletin* 56(3):761-772 (2000).

Millar, "Gonadotropin-Releasing Hormones and Their Receptors," *Reproductive Medicine: Molecular, Cellular and Genetic Fundamentals*, Bart C.J.M. Fauser (Ed.), The Parthenon Publishing Group, New York, Chapter 1, pp. 199-223 (2003).

Nestor, Jr., "Luteinizing Hormone Releasing Hormone Analogs in Control of Fertility and Gonadal Hormone Dependent Disease," *Annual Reports in Medicinal Chemistry*-23, Chapter 22, pp. 211-220 (1988).

Nestor, Jr., "Potent Gonadotropin Releasing Hormone Antagonists with Low Histamine-Releasing Activity," *J. Med. Chem.* 35:3942-3948 (1992).

O'Sullivan et al., "Comparison of Two Methods of Preparing Enzyme-Antibody Conjugates: Application of These Conjugates for Enzyme Immunoassay," *Analytical Biochemistry* 100:100-108 (1979).

Ojasoo et al., "Two Approaches to Structure-Activity Relationships in the Field of Sex-Steroids and Their Analogs," *Molecular Structure and Biological Activity of Steroids*, Chapter 4, pp. 157-207 (1992).

Pavlou et al., "Combined Administration of a Gonadotropin-Releasing Hormone Antagonist and Testosterone in Men Induces Reversible Azoospermia without Loss of Libido," *J. Clin. Endocrinol. Metabol.* 73(6):1360-1369 (1991).

Rahimpour et al., "Design, Synthesis, and Evaluation of a Long-Acting, Potent Analogue of Gonadotropin-Releasing Hormone," *J. Med. Chem.* 44:3645-3652 (2001).

Raynaud & Ojasoo, "The Relevance of Structure-Affinity Relationships in the Study of Steroid Hormone Action," *Steroid Hormone Receptors: Structure and Function,* Elsevier Science Publishers B.V., H. Eriksson & J.-A. Gustaisson (Ed.), pp. 141-170 (1983).

Russell-Jones et al., "Synthesis of LHRH Antagonists Suitable for Oral Administration via the Vitamin $B_{12}$ Uptake System," *Bioconjugate Chem.* 6:34-42 (1995).

Seal & Doe, "Vertebrate Distribution of Corticosteroid-Binding Globulin and Some Endocrine Effects on Concentration," *Steroids* 5:827-841 (1965).

Siiteri et al., "The Serum Transport of Steroid Hormones," *Recent Progress in Hormone Research* 38:457-510 (1982).

Swerdloff et al., "Suppression of Spermatogenesis in Man Induced by Nal-Glu Gonadotropin Releasing Hormone Antagonist and Testosterone Enanthate (TE) Is Maintained by TE Alone," *J. Clin. Endocrinol. Metabol.* 83(10):3527-3533 (1998).

Thau, "Luteinizing Hormone-Releasing Hormone (LHRH) an Its Analogs for Contraception in Women: A Review," *Contraception* 29(2):143-162 (1984).

Westphal, "Steroid-Protein Interaction: From Past to Present," *J. Steroid Biochem.* 19(1):1-15 (1983).

Azziz R. et al., "Leuprolide and Estrogen Versus Oral Contraceptive Pills for the Treatment of Hirsutism: a Prospective Randomized Study," *Journal of Clinical Endocrinology and Metabolism*, 80(12):3406-3411 (1995) (Abstract).

Irahara M. et al., "Efficacy of Every-Other-Day Administration of Conjugated Equine Estrogen and Medroxyprogesterone Acetate on Gonadotropin-Releasing Hormone Agonists Treatment in Women With Endometriosis," *Gynecologic and Obstetric Investigation*, 52:217-222 (2001) (Abstract).

Vincze B. et al., "Antitumour Effect of a Gonadotropin-Releasing-Hormone Antagonist (MI-1544) and its Conjugate on Human Breast Cancer Cells and Their Xenografts," *Journal of Cancer Research and Clinical Oncology, Springer International, Berlin, DE,* 120(10):578-584 (1994) (Abstract).

Ben-Yehudah A. et al., "Administration of L-GnRH-PE66 Efficiently Inhibits Growth of Colon Adenocarcinoma Xenografts in Nude Mice," *Int. J, Cancer,* 92:263-268 (2001) (Abstract).

Chengalvala M. V. et al., "GnRH Agonists and Antagonists in Cancer Therapy," *Curr. Med. Chem.-AnticancerAgents,* 3(6):399-410 (2003).

* cited by examiner

GONADOTROPIN RELEASING HORMONE ANALOGUES CONJUGATES WITH STEROID HORMONES

This application is a national stage application of PCT/GB2004/001478 under 35 U.S.C. §371 and claims the priority benefit of British Patent Application GB 0307777.3 filed Apr. 4, 2003.

This invention relates to conjugate compounds and in particular to gonadotropin-releasing hormone conjugate compounds.

Gonadotropin-releasing hormone (GnRH) is a neuroendocrine hormone involved in the control of reproduction, triggering the release of the gonadotropins, luteinizing hormone (LH) and follicle stimulating hormone (FSH).

GnRH analogues are extremely useful pharmacological agents, both in the investigation of the hypothalamic-pituitary axis and in the manipulation of gonadotropins for the treatment of hormone-dependent conditions. Most of the GnRH agonists and antagonists are peptide molecules consisting of about 9 or 10 amino acids, typically containing unnatural amino acids to modify receptor binding affinity, receptor activation, and to reduce proteolysis.

GnRH analogues have a range of clinical applications including treatment of hormone-dependent cancer, benign prostatic hypertrophy, endometriosis, uterine fibroids, premenstrual syndrome, polycystic ovarian syndrome, hirsutism, acne vulgaris, precocious puberty, acute intermittent porphyria, cryptoorchidism, delayed puberty and fertility treatment (Millar 2003).

In addition, GnRH analogues can be effective contraceptive agents. GnRH antagonists act by inhibiting ovulation when administered at the time of the LH surge; however the timing of dose is crucial and a short delay (hours) is sufficient to abolish any effect[2,4,6,7]. Alternatively corpus luteum function can be suppressed by GnRH antagonist treatment during the luteal phase[5] to inhibit the progression of early pregnancy. GnRH agonists can also inhibit gonadotropin release but by receptor desensitisation, which requires lower doses. In order to achieve inhibition of gonadotropin release, proportionally higher levels of antagonists compared with GnRH agonists are required due to the high receptor occupation required at the GnRH-receptor (GnRH-R).

Current female hormonal contraception employs supraphysiological doses of steroid hormone analogues to suppress gonadotrope secretion. Since peripheral tissues are exposed to the same levels, various side effects may result[1]. The development of male hormonal contraception is based on the same principle in combination with androgen replacement and faces the problems of similar side effects. Thus GnRH antagonists have the potential to form the basis of male and female contraceptives combined with gonadal steroid hormone replacement[1,3,7,12,18].

One of the major problems associated with long-term GnRH analogue treatment is the reduction in gonadal sex steroid hormones. Hormone replacement therapy is therefore required to prevent side effects such as hypoestrogenic bone loss in women and to maintain secondary sex characteristics in men.

An additional difficulty associated with GnRH analogue treatment is the rapid degradation of orally administered GnRH analogues in the gastrointestinal tract. Furthermore, GnRH analogues have a relatively short half-life in the circulation as they are excreted via the kidney, often on the first pass ($t_{1/2}$ of 1-7 minutes). These difficulties led to the development of slow-release injectable depot preparations to maintain effective in vivo concentrations of the GnRH analogues.

Currently, GnRH peptide antagonists are administered by injection. Endeavours are underway to develop non-peptide antagonists and orally active GnRH antagonists. The conjugation of GnRH analogues to haptens such as vitamin $B_{12}$, which is actively taken up into the gastrointestinal tract, offers the potential of conferring oral activity to peptide antagonists[15]. GnRH antagonists have previously been modified to include additional functional moieties. For example conjugation of GnRH to an emodin moiety[22] or conjugation of vitamin $B_{12}$ to antide to potentially enhance oral uptake[15,20,21] had been reported. Although oral administration of the vitamin $B_{12}$ conjugate had shown some increased uptake[21], no increase in the half-life of these components was demonstrated.

Many hormones are bound to plasma proteins in the circulation. This is thought to serve a variety of functions, including protecting them from renal clearance and metabolic degradation, thus extending their circulatory half-life[19].

There are two main circulatory steroid binding proteins in humans and most old world primates, cortisol binding globulin (CBG) which binds cortisol and progesterone, and sex hormone binding globulin (SHBG)[8] which binds testosterone and oestradiol. Hystricomorph rodent species such as guinea pigs also have a progesterone binding globulin (PBG) which specifically binds to progesterone.

Steroid binding to high molecular weight plasma proteins prevents their renal and metabolic clearance, in addition to inhibiting their entry into cells to interact with nuclear receptors. Thus the effective concentration of steroids in the circulation is determined by the unbound fraction (about 2% in humans), in a state of equilibrium with the bound fraction[16,19].

We have now shown that conjugating a GnRH analogue to a hormone moiety, or to a hormone derivative, extends the plasma half-life and improves the pharmacokinetics and pharmacodynamics of the GnRH analogue.

Without wishing to be bound by theory, we believe that the hormone or hormone derivative component of the conjugate compound binds to a plasma hormone binding protein which acts as a store for the GnRH analogue, and releases the GnRH analogue in a slow and continuous manner. Sequestration of the conjugate through binding to plasma proteins may "protect" the drug from excretion and from metabolism into inactive forms, thereby prolonging the half-life of the GnRH analogue.

We have shown that formation of a GnRH analogue-hormone conjugate extends its half-life and its duration of activity, reducing the dose of a GnRH analogue required for a biological effect. This also enables the conjugate to be administered a significant period before the antagonism is required, and to lower the frequency and amount of GnRH analogue administration, thus potentially reducing any side-effects of the treatment.

Furthermore, since the conjugate combines both a GnRH analogue and a functional steroid sex hormone in a single molecule, treatment with a GnRH analogue conjugated to a steroid sex hormone could reduce or alleviate the need for hormone replacement therapy.

A first aspect of the invention provides a compound comprising a GnRH analogue conjugated to a hormone moiety, or a derivative thereof, which is able to bind to a plasma hormone binding protein.

By GnRH we mean the decapeptide pGlu-His-Trp-Ser-Tyr-Gly-Leu-Arg-Pro-Gly-NH$_2$, in which the pGlu is pyroglutamate.

By "GnRH analogue" we include any molecule, whether a peptide or non-peptide molecule, that binds to the GnRH receptor. Binding of a molecule to the GnRH receptor can readily be determined by a person of skill in the art, for example using a receptor binding assay or whole cell binding assay such as described below in Example 1.

Typically, a peptide GnRH analogue is a peptide having between 6-12 amino acid residues. More preferably, a peptide GnRH analogue has 7, 8, 9, 10 or 11 amino acid amino acid residues. Yet more preferably, a peptide GnRH analogue has 9 or most commonly 10 amino acid residues.

Peptide GnRH analogues typically include at least one modified, ie non-naturally occurring, amino acid residue. GnRH agonists are generally produced by modifying the amino acids in positions 6 and 10 of the native GnRH decapeptide structure, whereas alteration of positions 1, 2, 3, 5, 6, 8, and 10 generally results in antagonism (Thau 1984).

Millar (2003) discusses the structure of GnRH and its receptor, as well as GnRH analogues which may be suitable for use in the present invention. The entire disclosure of Millar (2003) relating to GnRH and GnRH analogues is incorporated herein by reference.

In an embodiment, the GnRH analogue is a GnRH antagonist. GnRH antagonists are typically peptide molecules with a modified GnRH structure which bind to and block GnRH receptor (GnRH-R) activation or signalling.

By "GnRH antagonist" we include the meaning of any GnRH analogue, whether peptide or non-peptide, which inhibits, reduces or prevents signalling of the GnRH receptor. Inhibition, reduction or prevention of GnRH-R signalling can readily be determined by a person of skill in the art, for example using an inositol phosphate production assay such as described below in Example 1.

Millar et al (2000) discuss GnRH antagonists which may be suitable for use in the present invention. The entire disclosure of Millar et al (2000) relating to GnRH antagonists is incorporated herein by reference.

When no amino acid is specified for a particular position, it indicates that the same amino acid residue as in naturally occurring GnRH is present at that position.

The following abbreviations for the non-naturally occurring amino acids are used: AcD-Nal—acyl D-napthylalanine; D-Cpa—D-chlorophenylalanine; D-Pal—D-pyridylalanine; D-Lys—D-lysine; D-Ala—D-alanine; Ac-ΔPro—acyl delta-proline; D-Fpa—D-fluorophenylalanine; D-Trp—D-trytophan; Lys(Nic)—lysine nicotinamide; and iPr-Lys-isopropyl lysine.

The most preferred GnRH antagonists are Cetrorelix (Asta Medica AG), Ganirelix (Organon), Abarelix (Praecis Pharmaceuticals), Antide (Ares Serono SA), Teverelix (Ardana), FE200486 (Ferring) and Nal-Glu (NIH). The structure of these GnRH antagonists is shown in FIG. 8.

Other suitable GnRH antagonists include A-75998, A-76154 and A-84861 (originated by Abbott Laboratories); D-26344 and D-63153 (originated by ASTA Medica AG); ramorelix (originated by Aventis AG); degarelix (originated by Ferring Research Institute (UK)), NBI-42902 (originated by Neurocrine Biosciences Inc); Org-30850 (originated by Organon), detirelix (originated by Roche Bioscience); iturelix (originated by Serono SA); TAK-013 and TAK810 (originated by Takeda Chemical Industries Ltd); AN 207 (originated by Tulane University); the Pfizer GnRH antagonist; the Merck GnRH antagonist; and the Weizmann GnRH antagonist. See also the following reviews: Goulet (1995) *Ann. Reports Med. Chem.* 30, 169-178; Nestor & Vickery (1988) *Ann. Reports Med. Chem.* 23, 211-220; and Dutta & Barrington (1985) *Ann. Reports Med. Chem.* 20, 203-214, all of which are incorporated herein by reference.

Other suitable peptide GnRH antagonists include

AcD-Nal-D-Cpa-D-Pal-Ser-Arg-D-Lys-Leu-Arg-Pro-D-Ala-NH$_2$;

Ac-ΔPro-D-Fpa-D-Trp-Ser-Tyr-D-Lys-Leu-Arg-Pro-Gly-NH$_2$;

AcD-Nal-D-Cpa-D-Pal-Ser-Arg-D-Lys-Lys-Leu-Arg-D-Ala-NH$_2$;

D-Pal-Ser-Arg-D-Lys-Leu-Arg-Pro-D-Ala-NH$_2$;

AcD-Nal-D-Cpa-D-Pal-Ser-Arg-D-Lys-Lys-Arg-Pro-D-Ala-NH$_2$;

[D-Pyr$^1$, D-Phe$^2$, D-Trp$^{3,6}$]GnRH (see Rahimipour et al);

D-Lys$^6$Antide; Lys$^5$Antide; and Lys$^8$Antide.

Antide and its derivatives are described in Russel-Jones et al (1995) and WO 94/28015 (Biotech Australia Pty. Ltd). The entire disclosure of Russel-Jones et al and WO 94/28015 relating to GnRH antagonists, GnRH analogue conjugate compounds and their formation is hereby incorporated herein by reference.

Non-peptide GnRH antagonists which may be suitable for use in the present invention are described in WO 95/28405; WO 96/24597; WO 97/41126; WO 99/33831; WO 00/00493; WO 00/56739 and WO 01/78780 (Takeda Chemical Industries, Ltd) and WO 02/02533 (Yamanouchi Pharmaceutical Co., Ltd). The entire disclosure of these publications relating to GnRH antagonists, their formation, and use, is hereby incorporated herein by reference.

Further GnRH analogues, which may be useful in this invention, include those described in the following U.S. Pat. Nos. 3,813,382; 3,843,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135; 4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578; 4,143,133; 4,234,571, 4,253,997; 4,292,313; and 4,341,767. The entire disclosure of these US Patents relating to GnRH analogues, their formation, and use, is hereby incorporated herein by reference.

Yet further GnRH analogues which may useful in this invention include those described in the following U.S. Pat. Nos. 4,504,414; 4,677,193; 4,705,778; 5,064,939; 5,371,070 5,413,990; 5,502,035; 5,633,248; 5,756,497; 6,156,731 and 6,191,115; in EP 0 081 877 and EP 0 192 492; in the following published PCT applications WO 93/03058, WO 95/04541, WO 95/28405, WO 97/44321, WO 97/44339, WO 97/44041, WO98/03632, WO 98/55505, WO 99/21557, WO 99/41251, WO 99/41252, WO 99/46283 and WO 00/53178; and in GB 2 310 660. The entire disclosure of these publications relating to GnRH analogues, including both antagonists and agonists, their formation, and use, is hereby incorporated herein by reference.

In an embodiment, the GnRH analogue is a GnRH agonist.

By "GnRH agonist" we include the meaning of any GnRH analogue, whether peptide or non-peptide, which stimulates or activates signalling of the GnRH receptor. Stimulation or activation of GnRH receptor signalling can readily be determined by a person of skill in the art, for example using an inositol phosphate production assay such as described in Example 1. Incorporation of D isoform amino acids, particularly in position 6, increases the agonistic potency of GnRH analogues. Rahimpour et al (2001) report that over 3,000 GnRH analogues have been synthesised and evaluated for bioactivity. Most of the superagonists incorporate a D-amino acid in place of Gly in position 6, and many have an N-ethyl amide instead of the terminal Gly-NH2. These chemical modifications are reported to enhance the bioactive β-turn conformation of GnRH at the Gly-Leu bond and decrease the susceptibility of the peptide to proteolytic degeneration. Thus suitable GnRH agonists for use in the invention include GnRH analogues with either or both of these modifications.

In an embodiment, at least one of the amino acid residues of the GnRH analogue is D-lysine. Typically, the D-lysine is at position 6 of the analogue, that is the GnRH analogue is a [D-Lys$^6$]GnRH.

The most preferred GnRH agonists are Lupron (TAP), Zoladex (Zeneca), Supprelin (Roberts), Synarel (Searle), Triptorelin (Ferring) and Buserelin (Hoechst), each of which has a non-naturally occurring residue at position 6. The structure of these GnRH agonists is shown in FIG. 8.

Other suitable GnRH agonists include deslorelin (Balance Pharmaceuticals), ProMaxx-100 (Epic Therapeutics), avorelin (Mediolanum Farmceutici SpA), histrelin (Ortho Pharmaceuticals), and nafarelin (Roche Bioscience).

Peptide GnRH analogues may be made by any of the methods known to a person of skill in the art. For example, peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulfonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulfonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Alternatively, peptide GnRH analogues may be obtained by standard molecular biology techniques, provided that they can be encoded in a DNA molecule.

Peptide and non-peptide GnRH analogues suitable for use in the present invention are those which possess a suitable atom or functional group for conjugation to a hormone moiety or derivative thereof.

Suitable functional groups present on naturally occurring amino acid residues include the sulfhydryl group on a Cys residue, the hydroxyl group on Ser, Thr or Tyr residues, the ε-amino group on Lys residues, the carboxyl groups on Asp and Glu residues, the guanidino group on Arg residues, the amide groups on Asn and Gln residues, the imidazole NH group of His residues, the indole NH group of Trp residues, the C-terminal carboxyl group and the N-terminal amino group. The same functional groups are present on the D-isoforms of these amino acids residues.

Modified amino acids may also have suitable functional groups for conjugation to a hormone moiety. These include the hydroxyl group on hydroxyproline residues, the phosphate group on O-phosphoserine or O-phosphotyrosine residues, both the carboxyl groups on γ-carboxyglutamate residues, the ε-alkyl amino group on iPr-Lys residues and groups of citrulline and homocitrulline.

Further, the pyridyl N-atom of pyridylalanine residues and the secondary and tertiary guanidino N-atoms of N-alkylated Arg residues are suitable functional groups for conjugation to a hormone moiety by way of N-quaternisation. Again, the D- and L-isoforms may be present in the GnRH analogue.

Suitable functional groups for conjugation to the hormone moiety which are present on non-peptide GnRH analogues include keto, NH (as part of an amino, amido or ureidyl functionality), hydroxyl, sulfhydryl, carboxylic acid and tertiary amino groups.

Typically, the hormone moiety or derivative thereof which is conjugated to the GnRH analogue is one that binds to a plasma hormone binding protein in vivo.

Typically, the hormone binding protein is a globulin.

In an embodiment, the hormone moiety or derivative binds to a specific plasma hormone binding protein such as cortisol binding globulin (CBG), sex hormone binding globulin (SHBG), and, in some species, progesterone binding globulin (PBG). Typically, the hormone moiety or derivative thereof also binds to serum albumin (HSA). For the avoidance of doubt, in the context of the invention, HSA is a plasma hormone binding protein.

By "derivative" of a hormone moiety we include the meaning that the derivative has been modified from the structure of the hormone moiety found in nature. It may have been modified, for example, to provide a new or improved site of conjugation to the GnRH analogue, or to improve its stability, or its activity. However, the hormone derivative, as defined herein, will not have completely lost its ability to bind to a plasma hormone binding protein. It will be appreciated that the derivative may or may not itself have hormonal activity.

In a preferred embodiment, the hormone moiety is a steroid hormone moiety.

Steroid hormone moieties and derivatives thereof suitable for use in the present invention are those which possess a suitable atom or functional group for conjugation to a GnRH analogue.

Typically, steroid hormones have either a hydroxyl group or a keto group at the 3 position. Many of the steroid hormones have either a hydroxyl group or a keto group at the 17 position. A number of the steroid hormones have a hydroxyl group at the 11 position. Some of the steroid hormones have a hydroxyl group at the 21 position.

Preferably, the steroid hormone moiety is estradiol, progesterone, cortisol, corticosterone, estrone, testosterone and dihydroxytestosterone (DHT).

Steroid hormone derivatives include those which have been modified by adding a hydroxyl group at position 11, 17 or 21. Suitable progesterone derivatives include 11α-hydroxyprogesterones and 21-hydroxyprogesterones.

It will be appreciated that derivatives of steroid hormones which are steroids but which no longer have hormonal activity may be used provided that they bind to a plasma hormone binding protein.

The functional groups required for steroid hormones to bind to a plasma hormone binding protein are known to a person of skill in the art. For example, structural investigations using substituted steroids have demonstrated that in order to interact with SHBG, a steroid must contain a 17 β-hydroxyl group (Burton & Westphal (1972) and Cunningham et al (1981)). Several other features, such as the addition of a hydroxyl or a keto group at C11 have negative affects on binding affinity. Modification of carbon 2, 6, 9 and 11 in the steroid nucleus also reduced binding affinity (Cunningham et al (1981)).

For steroid binding to human CBG, the 20-oxo and 10β-methyl groups have been reported as being essential, and the 3-oxo and 4-ene are also important. Although the 11β, 17α-, and 21-hydroxy groups are relatively unimportant, hydroxyl groups impair binding at positions 11α, 6α, 6β, 12α, 14α, 16α and 19 (Mickelson et al 1981).

It is thus well within the ability of a person of skill in the art to conjugate a hormone moiety or derivative thereof to a GnRH analogue at a particular functional group so as to retain the ability of the hormone moiety to bind to a plasma hormone binding protein.

It is preferred if the linkers do not sterically hinder the interaction of the hormone with the plasma hormone binding protein or the GnRH analogue with a GnRH receptor. It is preferred if bulky and/or hydrophilic groups are not present in the linker proximal to the hormone moiety or GnRH analogue.

In some preferred embodiments of the present invention, the hormone moiety or derivative thereof retains its steroid activity, in whole or in part, when conjugated to the GnRH analogue. Alternatively, in other embodiments, it is preferred if the hormone moiety or derivative thereof does not retain any steroid activity when conjugated to the GnRH analogue.

In those embodiments in which hormone activity is desired, the functional group used for conjugation to the GnRH analogue is typically not one required for activity of that particular hormone or hormone derivative. Conversely, when hormone activity is not desired, the functional group used for conjugation to the GnRH analogue is typically one which is required for activity of that particular hormone or derivative thereof.

The functional groups required for the activity of the steroid hormones are known to a person of skill in the art (for example, steroid hormone-receptor structural relations are described for estrogens, glucocorticoids, mineralocorticoids, androgens, and metabolic analogues and antagonists in Duax et al (1989) *Advances in Drug Research* 18, 115-138; Aranyi (1982) *Hung. Biologia* (Budapest) 30, 145-169; Raynaud & Ojasoo (1983) *Nobel Symposium* 57, 141-170; Duax & Griffin (1989) *Alfred Benzon Symposium* 28, 62-77; Ojasoo et al (1992) *Mol. Struct. Biol. Act. Steroids*, pp 157-207, CRC, Boca Raton; and Duax & Griffin (1998) *NATO ASI series E: Applied Sciences* 352, 1-14, all of which are incorporated herein by reference. It is thus well within the ability of a person of skill in the art to conjugate a hormone moiety or derivative thereof to a GnRH analogue at a particular functional group so as to retain or eliminate activity of the hormone.

For example, as shown in Example 1, conjugation of a GnRH analogue to the 21 position of 21-hydroxyprogesterone maintains the progesterone activity in the conjugate compound. Conversely, if steroid hormone activity was to be eliminated, the GnRH could be conjugated to the keto group at the 3 position.

By the term "conjugated to" we include the meaning that a covalent bond is formed between an atom in the GnRH analogue and an atom in the hormone moiety, or that the GnRH analogue and the hormone moiety are both covalently bonded to the same linking group.

In a preferred embodiment, the conjugation between the GnRH analogue and the hormone moiety is cleavable, for example the conjugation includes an ester-linkage which is cleavable by an esterase, or an amide linkage which is cleavable by an amidase.

In an embodiment, the GnRH analogue and the hormone moiety are directly conjugated. Typically in this case an amino acid would be synthesised with the hormone moiety already attached, and this modified amino acid would be incorporated into a peptide GnRH analogue. For example, direct conjugation may arise through imine formation between the keto group on the hormone and the ε-amino group on Lys. The resulting imine may be hydrolytically unstable in vivo, thus giving rise to a conjugate having a short half-life. The half-life may be increased by reducing the imine to give an amine. Alternatively, direct conjugation may arise through Michael addition of the ε-amino group on Lys to an α,β-unsaturated ketone functionality in the hormone moiety (eg progesterone), or through reaction of a hormone moiety in which an OH group has been converted to a leaving group (eg a halide or a sulfonate ester) with a suitable nucleophilic group on a residue of the GnRH analogue (eg the ε-amino group on Lys or the β-OH group on Ser).

By "linking group" we mean a structure formed by one or more atoms that are not endogenous to either the GnRH analogue or the hormone moiety.

The linking group comprises one or more atoms, with the shortest route between the GnRH analogue and the hormone moiety or derivative thereof typically comprising 2 or 3 or 4 or 5 or 6 or 7 or 8 or 9 or 10 or more bonds.

The linking group may comprise a structure based upon one or more carbon atoms, optionally together with other atoms such as oxygen, nitrogen and/or sulfur, and the shortest route between the GnRH analogue and the hormone moiety or derivative thereof typically comprises 2 or 3 or 4 or 5 or 6 or 7 or 8 or 9 or 10 or more carbon atoms, optionally with at least one oxygen, nitrogen and/or sulfur atom.

Typically, the linking group is introduced by reacting a difunctional precursor linking moiety with the GnRH analogue and the hormone moiety, either simultaneously or in any sequential order. Alternatively, the linking group is formed by coupling together functional groups on structural fragments introduced by derivatisation of the GnRH analogue and/or hormone moiety.

Suitable linking groups include those represented by the formula $-A^1-D-A^2-$, wherein D represents, for example (a) alkylene, alkenylene or alkynylene (which latter three groups are optionally interrupted or terminated by NH, O or S, a carbocycle or a heterocycle and/or are optionally interrupted by —S—S—),
(b) a carbocycle, or
(c) a heterocycle, or D represents the structural fragment $-D^1-A^3-D^2-$, wherein $D^1$ and $D^2$ independently represent D as defined at (a) to (c) above; and $A^1$, $A^2$ and $A^3$ independently represent, for example, a direct bond, —C(O)—, —C(S)—, —S(O)—, —S(O)$_2$— or —P(O)$_2$—, provided that $A^3$ does not represent a direct bond when $D^1$ and $D^2$ are both independently terminated by O or NH at the point of connection to $A^3$. It will be clear that the $A^1$ and $A^2$ groups are linked to atoms endogenous to the GnRH analogue or hormone moiety, e.g. the N atom of a Lys residue in the GnRH analogue and the O atom of a hydroxyl group in the hormone moiety.

The linking group may be attached in either orientation to the GnRH analogue and the hormone moiety (i.e. the group $A^1$ of the linking group may be attached either to an atom of the GnRH analogue or an atom of the hormone moiety).

Alkylene, alkenylene or alkynylene groups as defined herein may contain between one and twelve (e.g. between one and eight, such as between one and six) C-atoms, and may be straight-chain or, when there is a sufficient number (i.e. a minimum of two for alkylene and alkenylene, and four for alkynylene) of carbon atoms, be branched-chain.

When used herein, the term "carbocycle" includes groups that are cyclic structures having a carbon skeleton and that comprise one or more rings of three or more members, for example 3- to 8-membered monocyclic ring systems, 7- to 12-membered bicyclic ring systems and 12- to 18-membered polycyclic (e.g. tri- or tetra-cyclic) ring systems. Further, each carbocycle may be fully saturated, part unsaturated or fully or partially aromatic in character. Examples of fully saturated carbocycles include cyclopentyl, cyclohexyl and cis- and trans-decalinyl and the like. Examples of part unsaturated carbocycles include cyclohexenyl and the like. Examples of partially aromatic carbocycles include indenyl and 1,2,3,4-tetrahydronaphthyl and the like. Examples of fully aromatic carbocycles include phenyl, naphthyl and the like.

When used herein, the term "heterocycle" includes groups that are a carbocyclic group, as defined above, in which one or more (e.g. one to three) of the ring C-atoms have been replaced by a corresponding number of heteroatoms, each heteroatom being independently selected from O, S and N (or, where relevant, NH). Examples of heterocyclic groups include azetidinyl, benzodioxanyl, benzodioxepanyl, benzodioxolyl, benzofuranyl, benzofurazanyl, benzimidazolyl, benzomorpholinyl, benzothiazolyl, benzothiophenyl, benzoxazolyl, chromanyl, cinnolinyl, coumarinyl, dioxanyl, furanyl, hydantoinyl, imidazolyl, imidazo[1,2-α]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfenyl, tetrahydropyranyl, tetrahydrofuranyl, thiazolyl, thienyl, thiochromanyl, triazolyl and the like Embodiments of the invention that may be mentioned include those in which the linking group is represented by the formula $-A^1-D-A^2-$ in which:

D represents $C_{1-6}$ alkylene, $C_{2-6}$ alkenylene or $-D^1-A^3-D^2-$;

$D^1$ represents $C_{2-6}$ alkylene optionally interrupted by —S—S—;

$D^2$ represents $C_{2-8}$ alkylene;

$A^1$ and $A^2$ both represent C(O);

$A^3$ represents C(O)NH.

Particular linking groups that may be mentioned include C(O)—(CH$_2$)$_2$—C(O) (succinyl) and C(O)—(CH$_2$)$_2$—S—S—(CH$_2$)$_2$—C(O)NH—(CH$_2$)$_6$—NHC(O).

Embodiments of the invention that may be mentioned include those in which the linking group connects an ε-amino group from a Lys residue in a peptidic GnRH analogue to a hydroxyl group on a hormone moiety.

Suitable methods and chemistry for conjugating a GnRH analogue to a hormone moiety or derivative thereof are known to those skilled in the art and include the method described in Example 1. Methods of conjugating a GnRH analogue to other chemical structures via a linker are described in Rahimipour et al (2001) and in Russell Jones et al (1995). Methods for making vitamin $B_{12}$ conjugates, which have application in forming the conjugates of the present invention, are described in McEwan et al (1999). The entire disclosure of these three documents related to the formation of chemical conjugates is hereby incorporated herein by reference.

The GnRH analogue may be conjugated to a hormone moiety or derivative thereof by any of the conventional ways of cross-linking molecules, such as those generally described in O'Sullivan et al *Anal. Biochem.* (1979) 100, 100-108. For example, one portion may be enriched with a thiol group and the other portion reacted with a bifunctional agent capable of reacting with the thiol group, for example the N-hydroxysuccinimide ester of iodoacetic acid (NHIA) or N-hydroxysuccinimidyl-3-(2-pyridyldithio)propionate (SPDP), a heterobifunctional cross-linking agent which incorporates a disulfide bridge between the conjugated species. Amide and thioether bonds, for example achieved with m-maleimidobenzoyl-N-hydroxysuccinimide ester, are generally more stable in vivo than disulfide bonds.

Further useful cross-linking agents include S-acetylthioglycolic acid N-hydroxysuccinimide ester (SATA) which is a reagent used for introducing a protected thiol functionality into compounds containing primary amino groups. Deprotection of the acetylated thiol group is achieved under mild conditions (Julian et al (1983) *Anal. Biochem.* 132, 68), ie by reaction with dimethylsuberimidate dihydrochloride and N,N'-o-phenylenedimaleimide.

In another embodiment, the GnRH analogue is conjugated to the hormone moiety via the N-terminal amine group.

Advantageously, the compound as described herein is less affected by metabolic or renal clearance in vivo than native GnRH, ie it has a longer half-life in vivo. This can readily be determined by a person of skill in the art, for example as described below in Example 1.

Preferably, the compound as described herein has a longer duration of activity than native GnRH in vivo. This can also readily be determined by a person of skill in the art, for example as described below in Example 1.

In a preferred embodiment, the compounds may have the general formula as shown in FIG. 1A or FIG. 1B.

The invention includes the compounds:

AcD-Nal-D-Cpa-D-Pal-Ser-Arg-D-Lys-Leu-Arg-Pro-D-Ala-NH$_2$ conjugated to 21-hydroxyprogesterone 21-succinate at the ϵ amine of D-Lys at position 6;

Ac-ΔPro-D-Fpa-D-Trp-Ser-Tyr-D-Lys-Leu-Arg-Pro-Gly-NH$_2$ conjugated to 21-hydroxyprogesterone 21-succinate at the ϵ amine of D-Lys at position 6;

AcD-Nal-D-Cpa-D-Pal-Ser-Arg-D-Lys-Lys-Leu-Arg-D-Ala-NH$_2$ conjugated to 21-hydroxyprogesterone 21-succinate at the ϵ amine of Lys at position 7;

D-Pal-Ser-Arg-D-Lys-Leu-Arg-Pro-D-Ala-NH$_2$ conjugated to 21-hydroxyprogesterone 21-succinate at the N-terminal amine;

AcD-Nal-D-Cpa-D-Pal-Ser-Arg-D-Lys-Lys-Arg-Pro-D-Ala-NH$_2$ conjugated to 21-hydroxyprogesterone 21-succinate at the ϵ amine of Lys at position 7;

[DLys$^6$]GnRH conjugated to 11α-hydroxyprogesterone 11-succinate at the ϵ amine group of the D-Lys at position 6;

[DLys$^6$]GnRH conjugated to 21-hydroxyprogesterone 21-succinate at the ϵ amine group of the D-Lys at position 6; and

[DLys$^6$]GnRH conjugated to β-oestradiol 17-succinate at the ϵ amine group of the D-Lys at position 6.

In an additional embodiment, the compound comprises a GnRH analogue conjugated to a hormone moiety or derivative thereof that is bound to a plasma hormone binding protein. The binding protein can be a hormone-specific binding protein such as CBG or SHBG, or can be HSA.

Compounds according to this embodiment are advantageous because they benefit from the protective effect of the binding protein immediately upon administration, reducing excretion of the GnRH analogue via the kidney on the first pass, thus further extending the half life and activity of the GnRH analogue.

A second aspect of the invention provides a pharmaceutical composition comprising a compound according to the first aspect of the invention and a pharmaceutically acceptable excipient, carrier or diluent.

In an embodiment, the pharmaceutical composition is suitable for oral administration.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

In an embodiment, the pharmaceutical composition or formulation is a unit dosage containing a daily dose or unit, daily sub-dose or an appropriate fraction thereof, of the active ingredient, ie a compound as described above in the first aspect of the invention.

In another embodiment, the pharmaceutical composition or formulation is a slow-release formulation, such as an injectable depot.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

At present, GnRH agonists are typically administered to a patient at about 100 μg per day, while GnRH antagonists are typically administered to a patient at about 1 mg per day. For oral and parenteral administration to human patients, the daily dosage level of the compounds of the invention will usually contain equivalent or lower levels of GnRH analogue, administered in single or divided doses.

Thus, for example, the tablets or capsules of the compound of the invention may contain from 50 μg to 1 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, being the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration which will be most appropriate for a particular animal. Conveniently, the formulation is a pharmaceutical formulation. Advantageously, for veterinary use, the formulation is a veterinary formulation.

A third aspect of the invention provides a compound according to the first aspect of the invention or a pharmaceutical composition according to the second aspect of the invention, for use in medicine.

Thus the compound or pharmaceutical composition is packaged and presented for use in medicine.

A fourth aspect of the invention provides a method of reducing the fertility of an individual comprising administering a compound according to the first aspect of the invention or a pharmaceutical composition according to the second aspect of the invention, to the individual.

It is appreciated that both GnRH agonist and GnRH antagonist conjugates can be used for reducing fertility in an individual by inhibiting the release of gonadotropin.

A fifth aspect of the invention provides the use of a compound according to the first aspect of the invention or a pharmaceutical composition according to the second aspect of the invention, in the preparation of a medicament for reducing the fertility of an individual.

Typically and preferably the individual to be treated is a human. However, the methods of the invention may be used to treat mammals, for example from the following species: cows, horses, pigs, sheep, cats and dogs, as well as other primates, old-world monkeys and new-world monkeys. Thus, the methods have uses in both human and veterinary medicine. In particular, in its veterinary applications, the conjugate may be used to create a state of castration in livestock, horses and domestic animals.

By "reducing fertility" in females, we include the meaning of reducing the likelihood of conception or a successful pregnancy, or of preventing conception or successful pregnancy. Thus the invention includes a method of female contraception.

By "reducing fertility" in males, we include the meaning of reducing testosterone levels to castrate levels Thus the invention includes a method of male contraception.

The methods of contraception described herein are reversible by cessation of administration of the compound, pharmaceutical composition or medicament.

A sixth aspect of the invention provides a method of combating a hormone-dependent disease or condition comprising administering a compound according to the first aspect of the invention or a pharmaceutical composition according to the second aspect of the invention, to an individual in need thereof.

By "combating" a disease or condition we include the meaning of alleviating symptoms of the condition (ie palliative use), or treating the disease or condition, or preventing the disease or condition (ie prophylactic use).

A seventh aspect of the invention provides the use of a compound according to the first aspect of the invention or a pharmaceutical composition according to the second aspect of the invention, in the preparation of a medicament for combating a hormone-dependent disease or condition in an individual in need thereof.

Hormone-dependent diseases or conditions suitable to be combated by the methods, uses, compounds and pharmaceutical composition of the invention include hormone-dependent cancer, benign prostatic hypertrophy, endometriosis, uterine fibroids, premenstrual syndrome, polycystic ovarian syndrome, hirsutism, acne vulgaris, precocious puberty, acute intermittent porphyria, cryptoorchidism and delayed puberty.

Hormone-dependent cancers suitable for treatment by the invention express GnRH receptors, and include breast cancer, prostate cancer, uterine cancer, endometrial cancer, ovarian cancer and testicular cancer.

An eighth aspect of the invention provides a method of combating infertility comprising administering a compound according to the first aspect of the invention or a pharmaceutical composition according to the second aspect of the invention, to an individual in need thereof.

A ninth aspect of the invention provides the use of a compound according to the first aspect of the invention or a pharmaceutical composition according to the second aspect of the invention, in the preparation of a medicament for combating infertility in an individual in need thereof.

The compounds of the invention can be used to combat infertility by inhibition of endogenous gonadotropin together with controlled administration of exogenous gonadotropin, especially in induction of ovulation in assisted reproduction techniques.

Thus the compounds of the invention have utility in in vitro fertilisation (IVF) techniques.

An tenth aspect of the invention provides a method of modulating the production of gonadotrophins or sex hormones in vivo comprising administering a compound according to the first aspect of the invention or a pharmaceutical composition according to the second aspect of the invention, to an individual.

By "modulating" we include increasing, reducing or inhibiting.

An eleventh aspect of the invention provides the use of a compound according to the first aspect of the invention or a pharmaceutical composition according to the second aspect of the invention, in the preparation of a medicament for modulating the production of gonadotrophins or sex hormones in vivo.

For example, in fertility treatment, the compounds of the invention can be used to inhibit completely endogenous hormone production, which is then replaced as desired either as part of the conjugate, or separately. The type, amount, frequency and duration of hormone replacement for use in fertility treatment is well known to a person of skill in this field, and in any event would be determined by a physician.

The conjugated compounds of the invention can also be used in vitro, or less likely in vivo, for differentiation or dedifferentiation of cells which express GnRH receptors, such as stem cells, and immune cells such as lymphocytes.

A twelfth aspect of the invention provides a method of modifying a GnRH analogue so that it has an increased in vivo half-life compared to GnRH, the method comprising conjugating the GnRH analogue to a hormone moiety, or a derivative thereof, which is able to bind to a plasma hormone binding protein.

A thirteenth aspect of the invention provides a method of modifying a GnRH analogue so that it has an increased duration of activity in vivo compared to GnRH, the method comprising conjugating the GnRH analogue to a hormone moiety, or a derivative thereof, which is able to bind to a plasma hormone binding protein.

Preferably, the GnRH analogue and the hormone moiety or derivative thereof, are conjugated via a linking group.

In an embodiment of the thirteenth and fourteenth aspects of the invention, the method includes binding the GnRH analogue which has been conjugated to a hormone moiety, or a derivative thereof, to a plasma hormone binding protein.

Typically, this binding is performed by contacting the GnRH analogue which has been conjugated to a hormone moiety, or a derivative thereof, with the plasma hormone binding protein in solution.

Preferences for the GnRH analogue, the hormone moiety or derivative thereof, linking group, and methods for performing the conjugation, are as described herein in Example 1 and above with respect to the first aspect of the invention.

In an embodiment, the method of the thirteenth and fourteenth aspects of the invention also includes the step of determining the in vivo half-life or duration of activity of the conjugated GnRH analogue. Typically, the method further comprises the step of comparing the determined in vivo half-life or duration of activity of the conjugated GnRH analogue with the in vivo half-life or duration of activity of GnRH.

Optionally, the method also includes the step of determining the in vivo half-life or duration of activity of GnRH. Alternatively, a previously determined value could be used.

The invention will now be described in more detail by reference to the following Figures and Examples.

FIG. 1A shows the structure of certain GnRH antagonist-steroid conjugates. Conjugates were produced by condensation of the side chain amine of D-Lysine in position six of the peptide, with the carboxyl of the 21-hydroxyprogesterone 21-hemisuccinate. The remainder of the residues in the peptide chain are represented by numbers 1-5 and 7-10. (21-hydroxyprogesterone 21-hemisuccinate is also known as deoxycorticosterone 21-hemisuccinate and 21-hydroxy-4-pregnene-3,20-dione 21-hemisuccinate.)

FIG. 1B shows the structure of GnRH agonist 11-hydroxyprogesterone 11-succinate.

FIG. 2 shows the GnRH receptor binding affinity. Displacement of $^{125}$I-GnRH agonist bound to whole COS-7 cells transfected with the human GnRH receptor. Peptide A GnRH antagonist (○), peptide A-progesterone conjugate (●), peptide B GnRH antagonist (□) and peptide B-progesterone conjugate (■).

Figure 8:
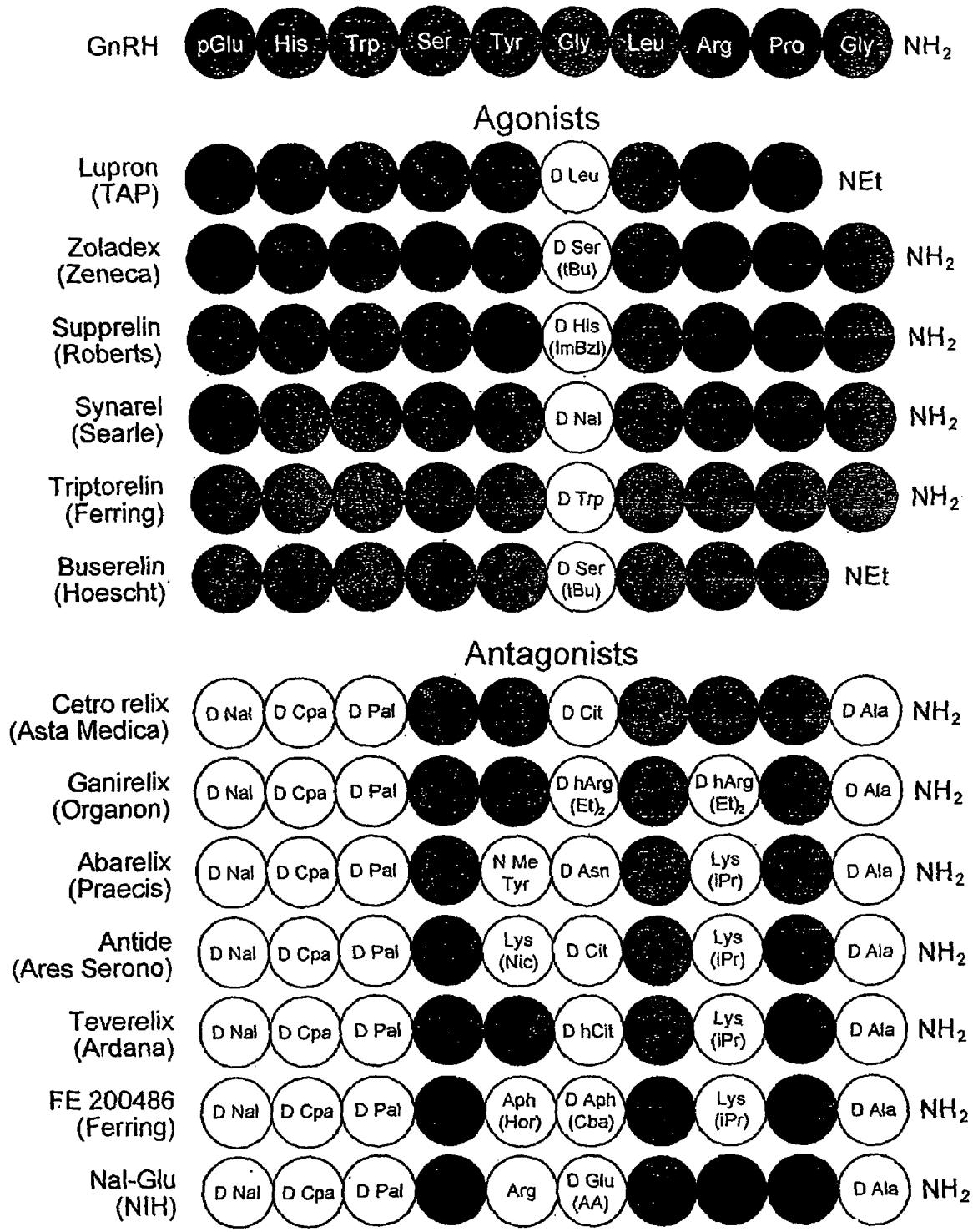
FIG. 8 shows the sequence of preferred GnRH analogues. The black circles indicate that the GnRH analogue has the same amino acid at that position as does GnRH itself.

The abbreviations used in FIG. 8 are as follows:

DSer(tBu): D-Ser t-butylether;

DHis(ImBzl): D-His benzylimidazole;

NEt: N-ethylamide;

DNal: D-napthtylalanine;

DCit: D-citrulline;

DhCit: D-homocitrulline;

DhArg(Et)$_2$: D-diethylhomoarginine;

NMeTyr: N-methyl tyrosine;

Aph(Hor):

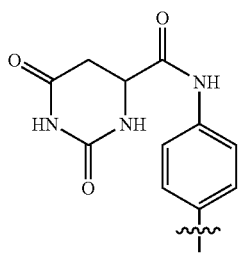

DAph(Cba):

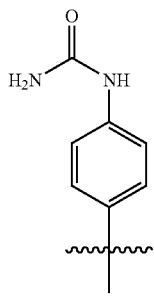

DGlu(AA):

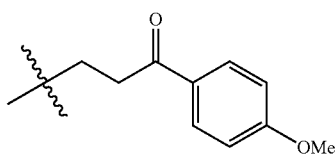

EXAMPLE 1

Synthesis and Properties of GnRH-Hormone Conjugates

Methods

Synthesis of GnRH Analogue-Steroid Conjugates

The conjugation method was adapted from Mattox, Litwiller and Nelson[9] and Rajkowski and Cittanova[14]. All chemicals were obtained from Sigma-Aldrich Company Ltd. (Poole, Dorset) with the exception of radiochemicals purchased from Amersham Pharmacia Biotech UK Limited (Little Chalfont, Buckinghamshire) and unless otherwise stated. The GnRH agonist [D-Lys$^6$]GnRH or the two GnRH antagonists kindly donated by J. Rivier (Salk Institute, La Jolla, Calif.)) [AcD-Nal$^1$, D-Cpa$^2$, D-Pal$^3$, Arg$^5$, D-Lys$^6$, D-Ala$^{10}$]GnRH, designated antagonist 1 and [AcD-Nal$^1$, D-Cpa$^2$, D-Pal$^3$, Arg$^5$, D-Lys$^6$, D-Ala$^{10}$]GnRH, designated antagonist 2, were dissolved in 0.1M phosphate buffer (pH 7.0) before addition of an equal volume of DMF. 20-fold excess steroid (11α-hydroxyprogesterone 11-hemisuccinate in the case of [D-Lys$^6$]GnRH or 21-hydroxyprogesterone 21-hemisuccinate for GnRH antagonist conjugation) was dissolved in anhydrous DMF with equimolar 1-hydroxybenzotriazole (HOBt) and N,N'-dicyclohexylcarbodiimide (DCC). The mixture was vortexed and left at room temperature for 1 hour. The steroid containing solution was transferred in aliquots of 50 µl into each of the peptide solutions. After adjustment to pH>7 with tributylamine, the peptide-steroid mixture was left at 4° C. for 20 hours.

Purification and Identification of Products

HPLC

An initial purification through a Sep-Pak C18 cartridge (Millipore UK Ltd., Harrow, Middlesex) with ethylacetate followed by hexafluropropanol/DMF (70:30) was carried out before HPLC and mass spectrometry analysis of products. Analytical RP-HPLC was carried out on a Novapak C18 column (4 µm beads, 3.9×150 mm) connected to a Beckman Coulter System Gold® LC125 pump and LC168 diode array detector. The buffer system was 0.1% TFA/water as buffer A and 0.1% TFA in acetonitrile as buffer B. The column was developed with a gradient of 10% to 100% buffer B over 30 mins at a flow rate of 1 ml/min.

Mass Spectrometry

Mass spectrometry was carried out on a Tofspec 2E MALDI-TOF mass spectrometer (Micromass UK Ltd.) with a matrix of alpha-cyano-4-hydroxycinnamic acid.

Cell Culture

COS-7 and COS-1 cells were maintained in DMEM containing 10% fetal calf serum, glutamine and penicillin/streptomycin (normal media). Cells were transfected with the human GnRH receptor (hGnRH-R) for whole cell receptor binding assay using Superfect transfection agent (Qiagen, Crawley, West Sussex) in optimem media (Invitrogen Life Technologies, Paisley, Scotland) for four hours. Transfected cells were assayed after a further 48 hours in normal media (see above).

Membrane binding assay of GnRH agonist-progesterone conjugates was carried out on COS-1 cells transfected with hGnRH-R. COS-1 cells in 100 mm dishes were washed twice in HEPES modified DMEM and transfected with 15 µg DNA in filter-sterilised DEAE dextran with HEPES buffered saline, penicillin/streptomycin and DMEM. After five hours incubation at 37° C., the media was removed and replaced with DMEM containing penicillin/streptomycin, 2% FCS and 2% chloroquine 10 mM and plates were incubated for a further one hour. The media was aspirated, cells were washed and normal media was added until assay 24 hours later.

A HEK293 stable cell line expressing the rat type I GnRHR developed in our laboratory was used for the inositol phosphate production assays. This cell line was maintained in DMEM containing 10% fetal calf serum, glutamine and penicillin/streptomycin with the addition of G418 at 500 µg/ml throughout culture. Where required, plates were coated with Poly-L-Lysine to enhance adherence to plasticware during assay.

Receptor Binding Assay

Membrane Binding Assay of GnRH agonist-Progesterone Conjugate:

Transfected COS-1 cells were washed in PBS, removed from plates and centrifuged at 1500 rpm for five mins to pellet cells. The PBS was aspirated and the cells were resuspended in homogenization buffer (20 mM Tris, 2 mM $MgCl_2$, pH 7.2), vortexed and left on ice for 10 minutes. The cell suspension was transferred to a 7 ml homogeniser (Jencons (Scientific) Ltd., Leighton Buzzard, Buckinghamshire) and plunged 15 times with a loose plunger and 15 times with a tight plunger. The homogenized cells were then centrifuged at 4° C. for 10 mins at top speed and the supernatant was removed with a vacuum pump. The remaining membrane pellet was resuspended in assay buffer (40 mM Tris, 2 mM $MgCl_2$, pH 7.4) and kept on ice. Pre-cooled 12 mm glass tubes were filled with 200 μl assay buffer, 50 μl cell membranes, 100 μM $^{125}I[His^5,D-Tyr^6]GnRH$ in assay buffer (approximately 120,000 CPM per tube) and 50 μl cold ligand (or assay buffer in Bo tubes) in increasing concentrations. Tubes were incubated for 2 hours on ice before addition of 3 ml ice-cold aqueous polyethylenimine 0.01% (PEE) and filtration through Whatman GG/C glass fibre filters (Whatman International Ltd., Maidstone, Kent) under vacuum (presoaked in 1% PEE). Filters were then counted immediately on a gamma counter.

Whole Cell Binding Assay of GnRH Antagonist-Progesterone Conjugates:

COS-7 cells were plated in 12 well plates and maintained in a 37° C. incubator for 24 hours in advance of assay. Cells were washed twice with PBS before addition of 500 μl HEPES modified in DMEM+0.1% BSA containing competing ligand and $^{125}I$ ligand ($^{125}I[His^5D-Tyr^6]GnRH$). Plates were washed twice in PBS and solubilised by addition of 500 μl 0.1M NaOH and shaking for 20 minutes. Samples were counted on a gamma counter.

Measurement of Total Inositol Phosphate Production

Rat type I GnRH receptive expressing HEK293 cells were plated out onto 12 well plates and incubated at 37° C., 5% $CO_2$ for 24 hours, then incubated in special DMEM containing 1% dialysed FCS (with glutamine and penicillin/streptomycin) and 1 μl/well of myo-$[2-^3H]$inositol for a further 48 hours. After aspiration of media and washing with incubation buffer, a further 500 μl buffer containing 10 mM LiCl was added to the plates and then incubated at 37° C. for 30 mins. 1 μM agonist was added to each well to a final concentration of 0.1 μM and the plates were incubated under the same conditions for a further 1 hour. The reaction was terminated with 500 μl 10 mM formic acid, incubated at 4° C. for 30 mins. Formic acid solutions were transferred to 12 mm plastic tubes containing 500 μl 50% AG-1× resin slurry (Bio-Rad Laboratories Ltd, Hemel Hempsted, Hertfordshire). Inositol phosphates were eluted by stepwise addition, vortex mixing and removal of distilled water (1 ml) and sodium tetraborate, sodium formate (1 ml, 5 mM, 60 mM). After addition of formic acid, ammonium formate (1 ml, 0.1M, 1M) and vortexing, 800 μl of the supernatant was counted with scintillation fluid.

Plasma Protein Binding Assay

Plasma protein binding was determined by the competitive binding of steroid conjugates, in the presence of $[1,2,6,7-^3H]$ progesterone or $[^3H]$cortisol, to pregnant guinea pig plasma or human pregnant serum respectively. 20 μl serum was diluted with 2 ml dextran-coated charcoal solution (0.25 g dextran T-70, 2.5 g charcoal decolorizing powder, activated acid washed [Merck Ltd., Lutterworth, Leicestershire] in 500 ml PBS) and incubated at room temperature. After 30 mins the suspension was centrifuged at 3000×g for 10 minutes, the supernatant was removed and the pellet was discarded. 100 μl of diluted serum was aliquoted into centrifuge tubes, followed by 1 pmol[$^3H$]steroid/100 μl PBS. 100 μl PBS (total binding) or 200 pmol/100 μl unlabelled competing ligand (specific binding) was added to diluted serum in duplicate. Tubes were vortexed and incubated at room temperature for 1 hour, then for an additional 15 minutes on ice. A further 750 μl dextran-coated charcoal suspension was added and incubated for 10 minutes on ice, followed by centrifugation at 4° C. for 5 minutes. The supernatant fluid was counted.

In Vivo Studies in the Male and Female Common Marmoset (*Callithrix Jacchus*)

Female marmoset studies: To identify the effective dose required to inhibit corpus luteum function, 1.0, 0.5 or 0.25 mg of GnRH antagonist-steroid conjugate was administered as subcutaneous bolus in 1 ml saline at two sites during mid-luteal phase. Progesterone concentrations were monitored by RIA. One 300 μl blood sample was withdrawn on the day prior to GnRH antagonist injection. Further blood samples of equal size were withdrawn at 0, 4 and 8 hours on day of injection and on the following 3 days. Blood samples were taken three times per week until the next ovulation.

Male marmoset studies: To determine duration of action at GnRH receptor, 0.5 mg GnRH antagonist-steroid conjugate was administered as subcutaneous bolus in 1 ml saline at two sites in six adult male marmosets. Testosterone concentrations were monitored by RIA. GnRH antagonist (0.5 mg) was administered as a subcutaneous bolus in 1 ml saline at two sites in three marmosets. Testosterone concentrations were monitored. One 300 μl blood sample was withdrawn on the day prior to GnRH antagonist injection and at 0 hours, 4 hours and 8 hours on the day of injection and on the following 3 days. Three further samples were taken during the subsequent week.

In Vivo Studies in the Male Rabbit

To determine biological half-life of GnRH agonist-progesterone conjugates, 0.5 ml saline containing approximately 10,000,000 cpm of iodinated [D-Ala$^6$]GnRH or [D-Lys$^6$] GnRH-progesterone conjugate was injected as an i.v. bolus into the ear vein of a male rabbit. Rabbits were sedated with 0.4 ml Aceprom 10 (Milborrow Animal Health, Republic of South Africa) injected intramuscularly 3-4 minutes before start of experiment. A repeat injection was carried out after 2 hours. 1 ml blood samples were collected in heparinized tubes from an indwelling cannula placed in a vein of the contralateral ear. Whole blood was counted directly to determine disappearance from circulation. All experiments were carried out in accordance with Republic of South Africa regulations.

Results

GnRH Receptor Binding

Figure 1A:
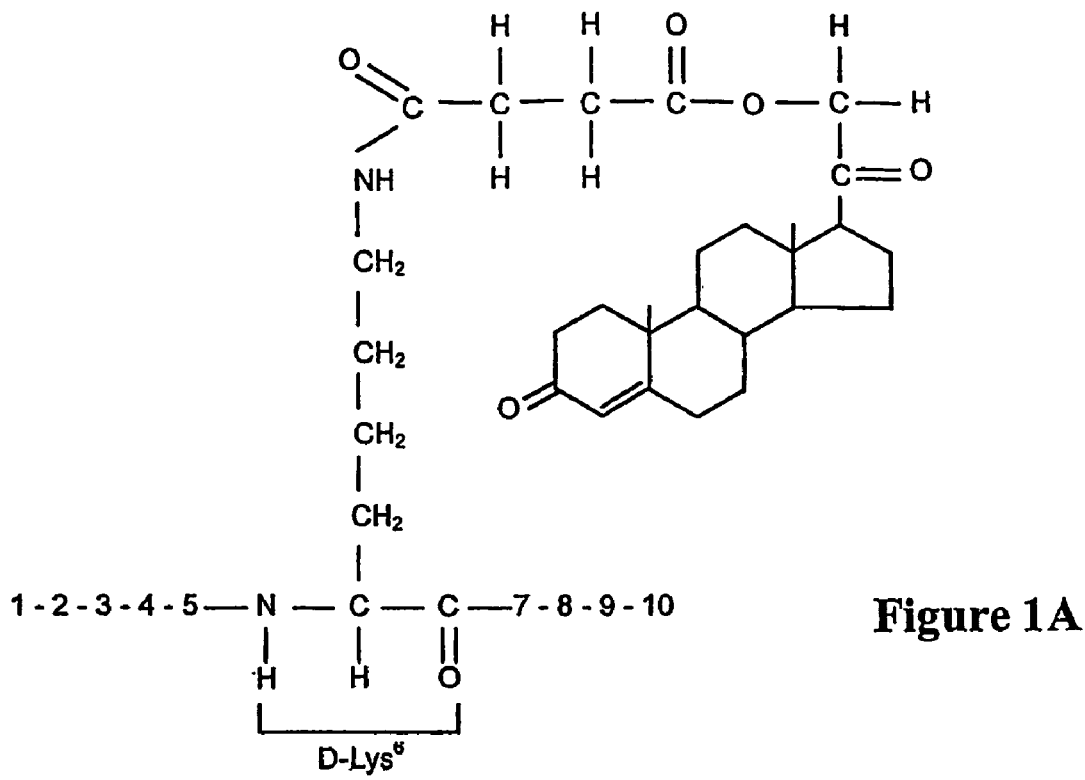
Figure 1B:
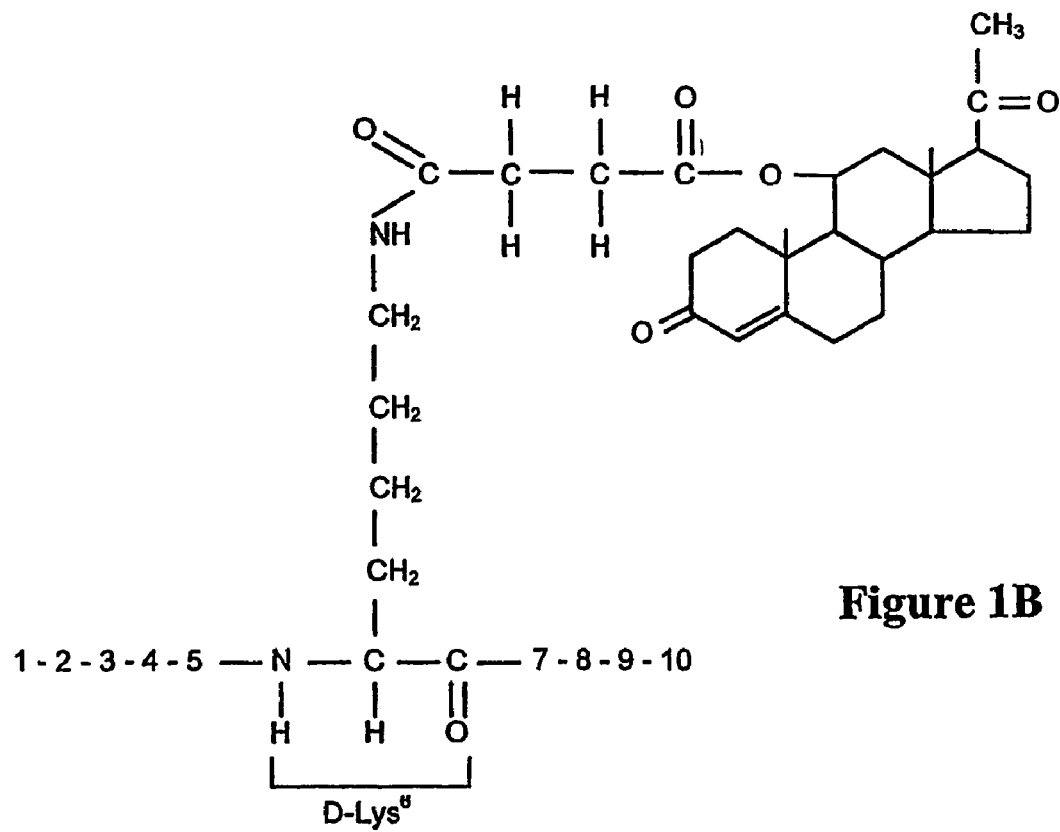
Figure 2:
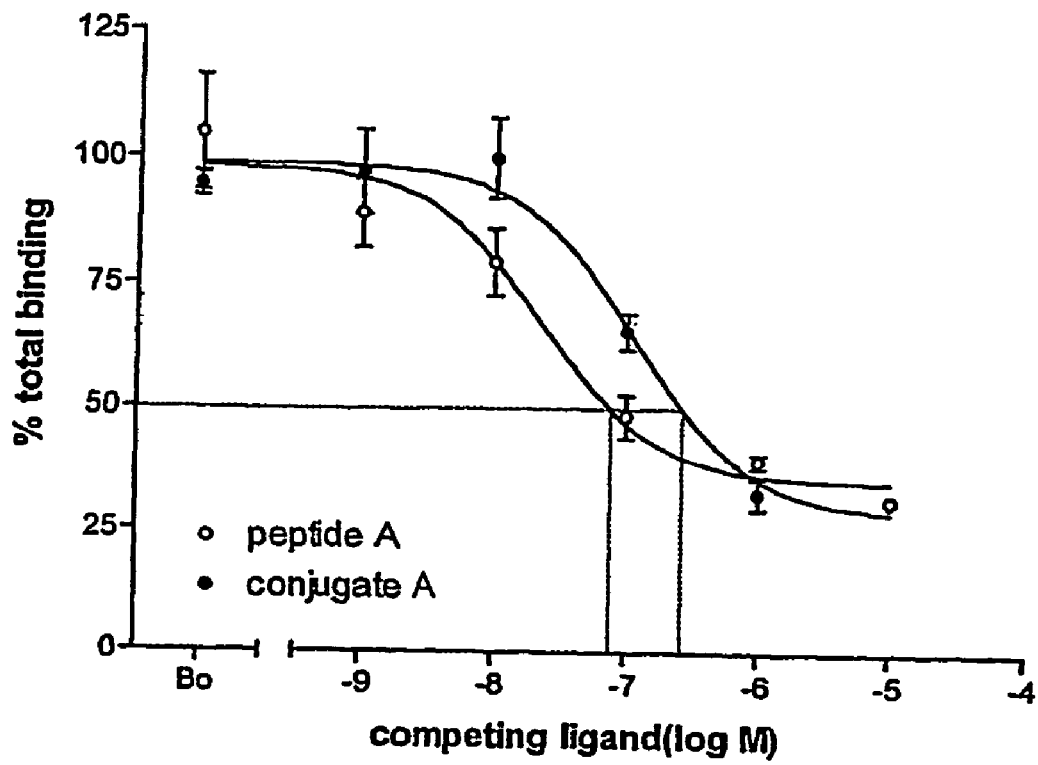
Figure 2:
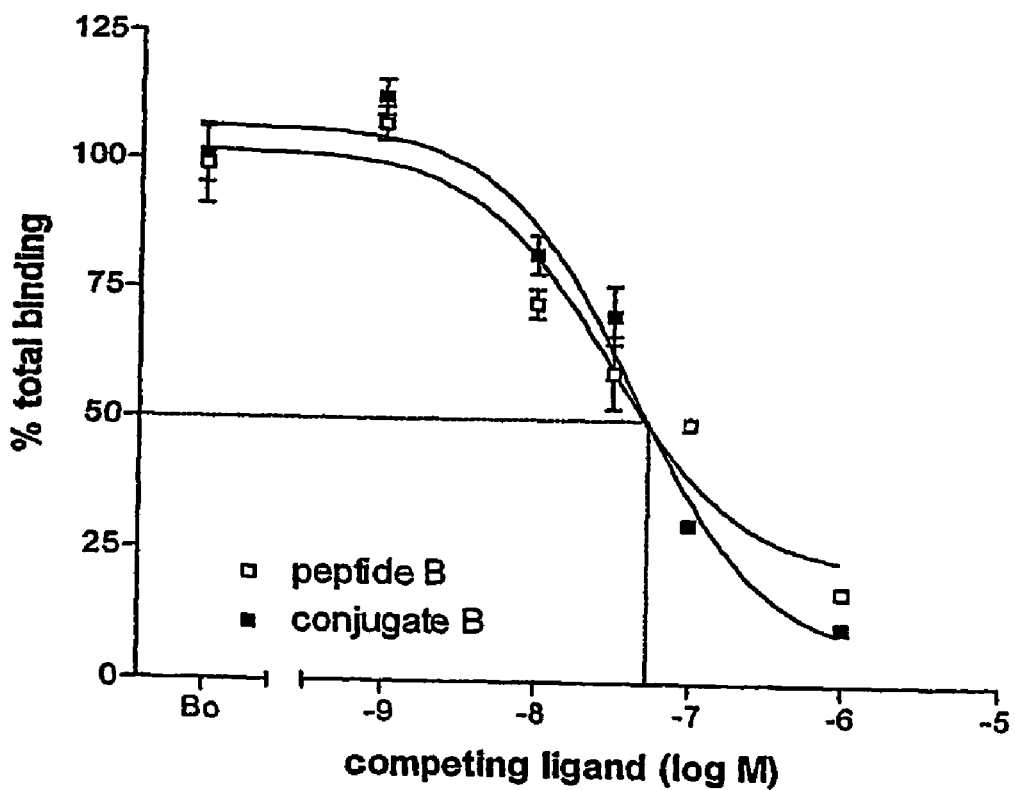

The GnRH agonist-progesterone conjugate bound to the type I human GnRH receptor with $ED_{50}$ of $2.9\pm1.2\times10^{-10}M$ (Standard error, n=1, data not shown). The GnRH antagonist A-progesterone and antagonist B-progesterone conjugates also bound to the receptor (FIG. 2) as shown by whole cell binding assay. The $ED_{50}$ of antagonist A-progesterone was $1.1\pm0.2\times10^{-7}M$ (n=4) compared with $1.6\pm0.4\times10^{-8}M$ (n=4) for the unmodified antagonist sequence (p<0.01, STT). The $ED_{50}$s for antagonist B and antagonist B-progesterone were $4.7\pm1.1\times10^{-8}M$ (n=4) and $1.1\pm0.3\times10^{-7}M$ (n=5) respectively (p<0.05, STT).

Inhibition of GnRH-Stimulated Inositol Phosphate Production

Figure 3:
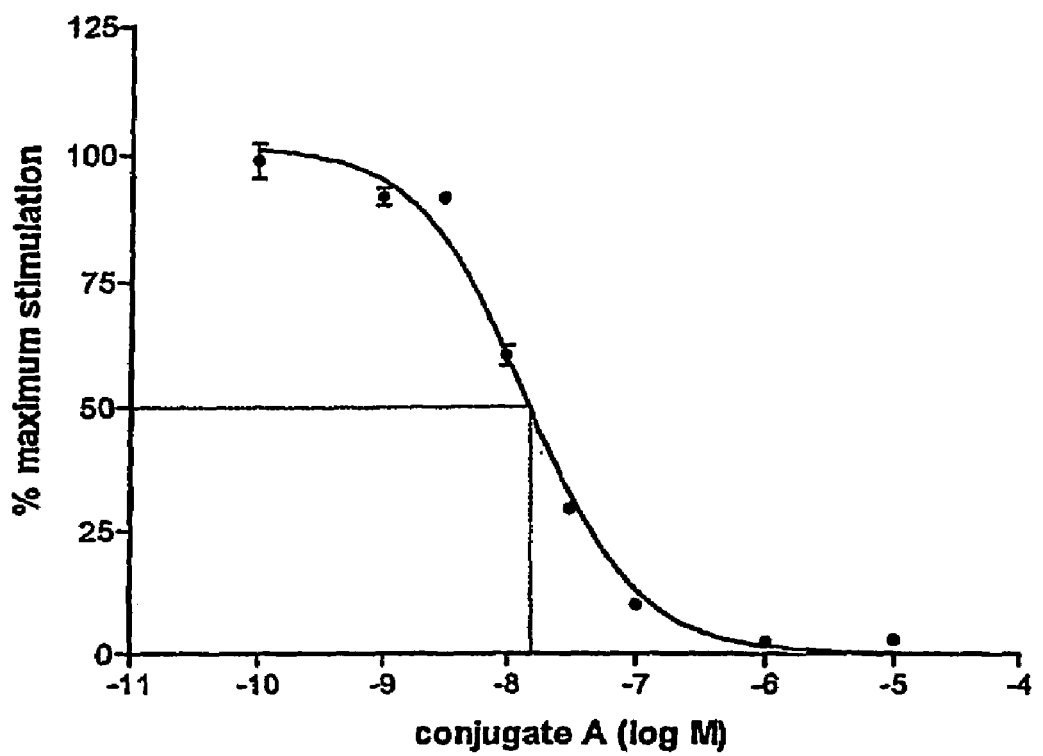
FIG. 3 shows the effects of peptide A-progesterone conjugate and peptide B-progesterone conjugate on mammalian GnRH (0.1 μM) stimulated inositol phosphate production in HEK 293 cells stably expressed the rat type I GnRHR.
Figure 3:
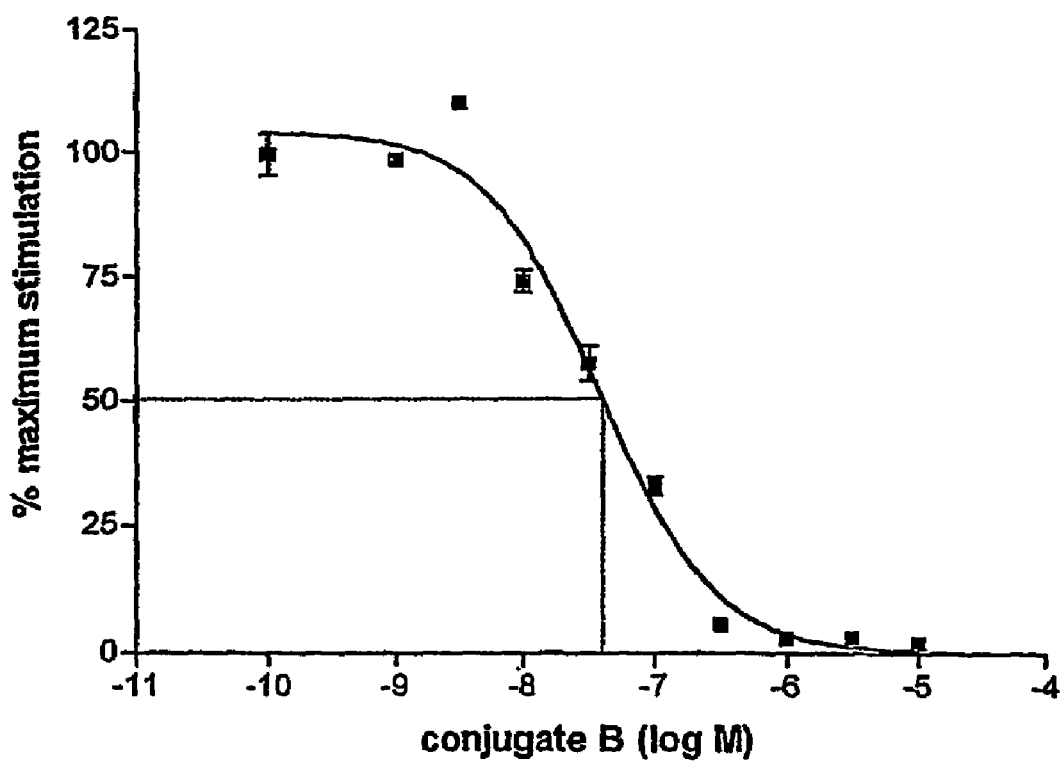
Figure 4:
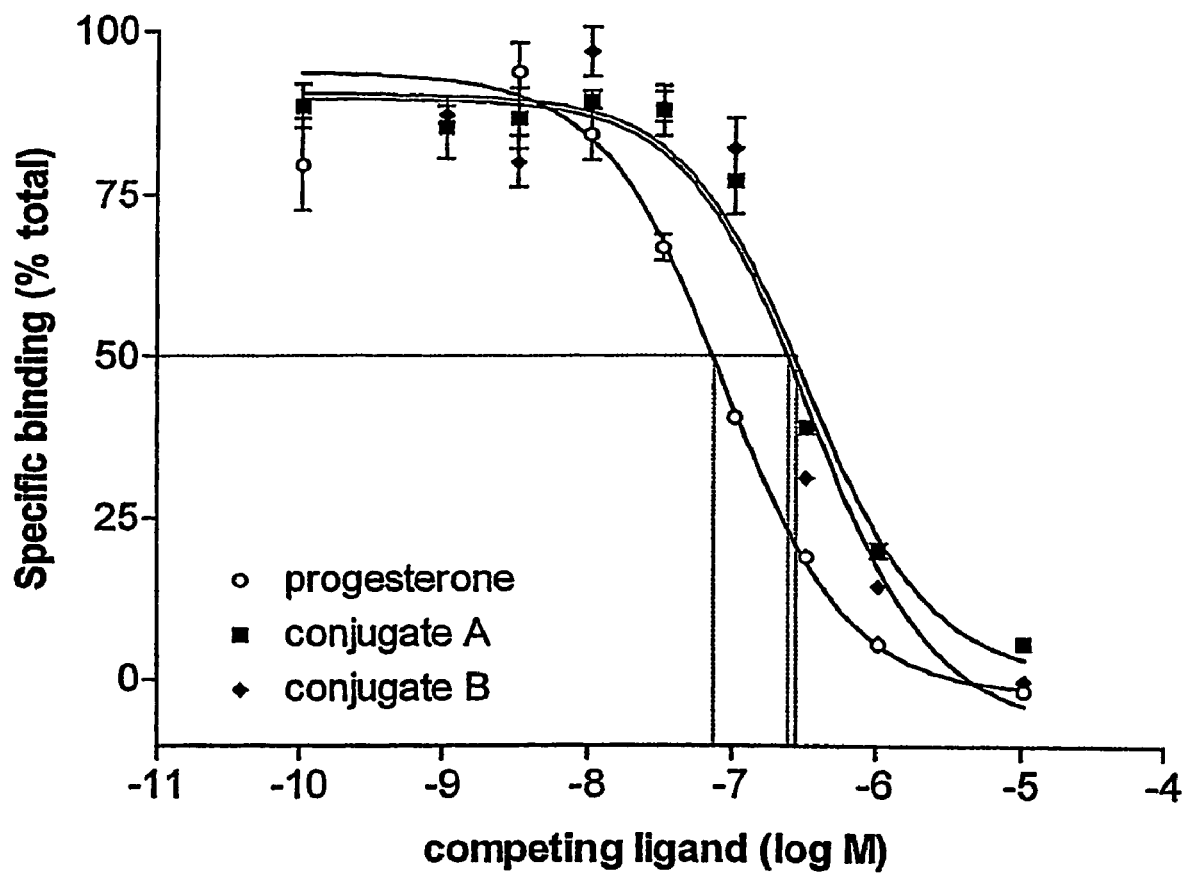
FIG. 4 shows the effects of progesterone (○), peptide A-progesterone (●) and peptide B-progesterone (♦) on the binding of [1,2,6,7-$^3$H]progesterone to pregnant guinea pig plasma, as measured with dextran-coated charcoal suspension.

The GnRH agonist-progesterone conjugate was able to stimulate inositol phosphate production with an $EC_{50}$ of $5.2\pm1.4\times10^{-10}M$ (n=2); this was not significantly different from the peptide alone (STT, p>0.05). GnRH antagonism of both antagonist A-progesterone and antagonist B-progesterone conjugates was confirmed by the inhibition of mammalian GnRH (0.1 µM) stimulated inositol phosphate production (FIG. 3). The $IC_{50}$ of antagonist A-progesterone and antagonist B-progesterone conjugates were not significantly different (p>0.05, STT).

Inhibition of GnRH-Stimulated Inositol Phosphate Production

The GnRH agonist-progesterone conjugate was able to stimulate inositol phosphate production with an $EC_{50}$ of to the $IC_{50}$ of $6.7 \pm 2.4 \times 10^{-9}$M (n=2) for unlabelled cortisol and $7.3 \pm 1.5 \times 10^{-8}$M (n=3) for progesterone (data not shown).

Activation of Progesterone

Assay of CAT enzyme activity revealed that all GnRH antagonist 21-hydroxyprogesterone 21-succinate conjugates were able to bind to and activate the progesterone receptor in T47D cells are measured by CAT enzyme activity. The potencies of all conjugates were similar to progesterone, with virtually no activation at 1 nM and increasing activity up to 1 µM. The 5 conjugates tested are as shown in Table 1, below:

TABLE 1

| | GnRH antagonist conjugates | | | | | | | | | |
|---|---|---|---|---|---|---|---|---|---|---|
| Amino Acid | 1 | 2 | 3 | 4 | 5 | 6 | 7 | 8 | 9 | 10 |
| GnRH | Glu | His | Trp | Ser | Tyr | Gly | Leu | Arg | Pro | Gly-NH₂ |
| Conjugate A | AcD-Nal | D-Cpa | D-Pal | Ser | Arg | D-Lys* | Leu | Arg | Pro | D-Ala-NH₂ |
| Conjugate B | Ac-ΔPro | D-Fpa | D-Trp | Ser | Tyr | D-Lys* | Leu | Arg | Pro | Gly-NH₂ |
| Conjugate C | AcD-Nal | D-Cpa | D-Pal | Ser | Arg | D-Lys | Lys* | Leu | Arg | D-Ala-NH₂ |
| Conjugate D | | | *D-Pal | Ser | Arg | D-Lys | Leu | Arg | Pro | D-Ala-NH₂ |
| Conjugate E | AcD-Nal | D-Cpa | D-Pal | Ser | Arg | D-Lys | Lys* | Arg | Pro | D-Ala-NH₂ |

The amino acid sequences of the antagonists tested shown aligned to mammalian GnRH for comparison. The following abbreviations are used: Glu; glutamic acid, His; histidine, Trp; tryptophan, Ser; serine, Tyr; tyrosine, Gly; glycine, Leu; leucine, Arg; arginine, Pro; proline, AcD-Nal; acyl D-napthylalanine, D-Cpa; D-chlorophenylalanine, D-Pal; D-pyridylalanine, D-Lys; D-lysine, D-Ala; D-alanine, Ac-ΔPro; acyl delta-proline, D-Fpa; D-fluorophenylalanine, D-Trp; D-trytophan.

$5.2 \pm 1.4 \times 10^{-10}$M (n=2); this was not significantly different from the peptide alone (STT, p>0.05). GnRHR antagonism of both antagonist A-progesterone and antagonist B-progesterone conjugates was confirmed by the inhibition of mammalian GnRH (0.1 µM) stimulate inositol phosphate production (FIG. 3). The $IC_{50}$ of antagonist A-progesterone and antagonist B-progesterone conjugates were not significantly different (p>0.05, STT) at $9.7 \pm 4.0 \times 10^{-8}$M (n=6) and $8.6 \pm 2.6 \times 10^{-8}$M (n=7) respectively. Neither the antagonist A-progesterone nor antagonist B-progesterone conjugate was found to activate inositol phosphate production alone (data not shown), confirming pure antagonism.

Competition for Plasma Protein Binding Site

Plasma protein binding was studied in pregnant guinea pig plasma because a high level of progesterone binding globulin (PBG) is present in this species. PBG was shown to bind [³H]progesterone in a specific manner and this binding was inhibited by unlabelled progesterone with an $IC_{50}$ of $9.6 \pm 1.8 \times 10^{-8}$M (n=4), by the antagonist A-progesterone conjugate with an $IC_{50}$ of $1.0 \pm 0.3 \times 10^{-6}$M (n=6) and by the antagonist B-progesterone conjugate with an $IC_{50}$ of $5.3 \pm 1.0 \times 10^{-7}$M (n=4). The specificity of this steroid-plasma protein interaction was demonstrated by a failure of cortisol to inhibit specific [³H]progesterone binding, since PBG will only bind progesterone. It was also shown that the agonist-progesterone conjugate could prevent [³H]cortisol binding to human pregnant serum (containing higher than normal concentrations of CBGH) with an $IC_{50}$ of $1.2 \pm 0.3 \times 10^{-6}$M (n=2) in comparison All five antagonists are conjugated to the same steroid, 21-hydroxyprogesterone 21-hemisuccinate in different positions marked by the asterisk. In conjugates A and B the site of conjugation is via the ε-amine of D-Lys in position 6. In conjugates C and E conjugation is via the ε-amine of lysine in position 7. In conjugate D the steroid is conjugated to the N-terminal amine of the D-Pal residue.

In Vivo Marmoset Studies

Studies in cycling adult female marmosets revealed a reduction in the duration of the luteal phase from $24.8 \pm 2.2$ (n=6) to 8 days in the animal receiving 1.0 mg antagonist A-progesterone conjugate and in the animal administered with 0.5 mg, with the reduction from $21.0 \pm 1.2$ (n=7) to 11 days. Ovulation was deemed to have taken place when the plasma concentration of progesterone reached 30 ng/ml. A transient reduction in plasma progesterone concentrations was also seen in the third marmoset receiving 0.25 mg antagonist A-progesterone conjugate, but full luteal regression and subsequent ovulation did not occur at this time.

Figure 5:
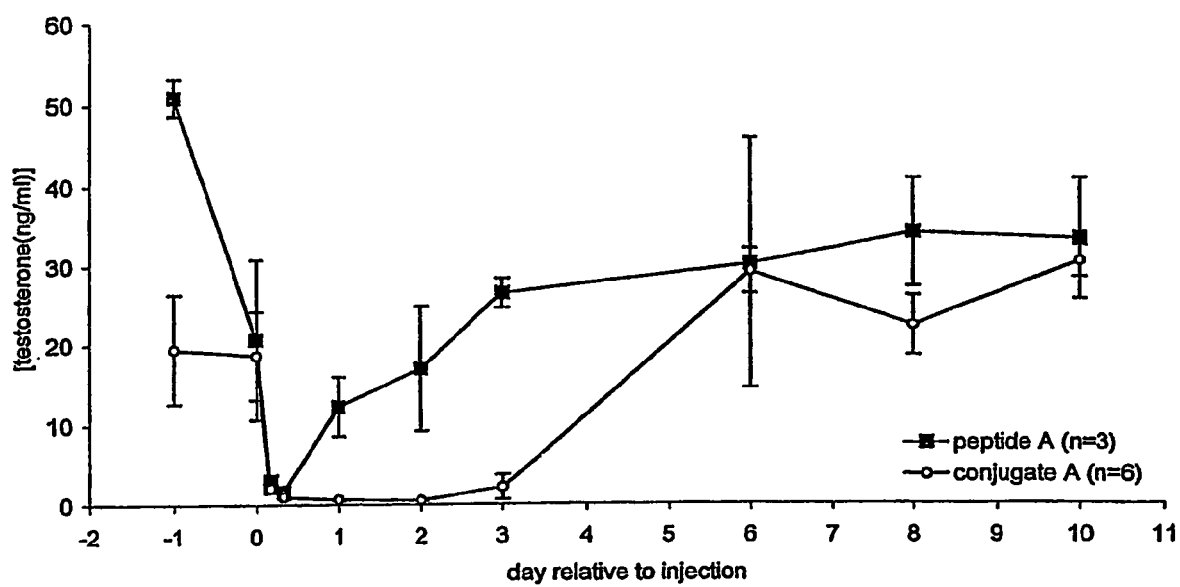
FIG. 5 shows the testosterone concentrations of male marmosets injected s.c. with either 0.5 mg peptide A-progesterone (○) or 0.5 mg peptide A (■).

Administration of 0.5 mg of peptide A to male marmosets (n=3) resulted in a rapid decline in plasma testosterone concentrations (FIG. 5). The reduction in testosterone concentration was maintained at 8 hours post-injection but increased by 24 hours. In comparison, 0.5 mg peptide A-progesterone conjugate (n=6) also rapidly decreased testosterone concentrations, however this was maintained until at least 72 hours post-injection (p<0.05 versus 24 hour post-injection) and recovered by day 6. The constraints of existing Home Office licensing prevented additional blood samples on days 4 and 5.

In Vivo Studies in the Male Rabbit

Figure 6:
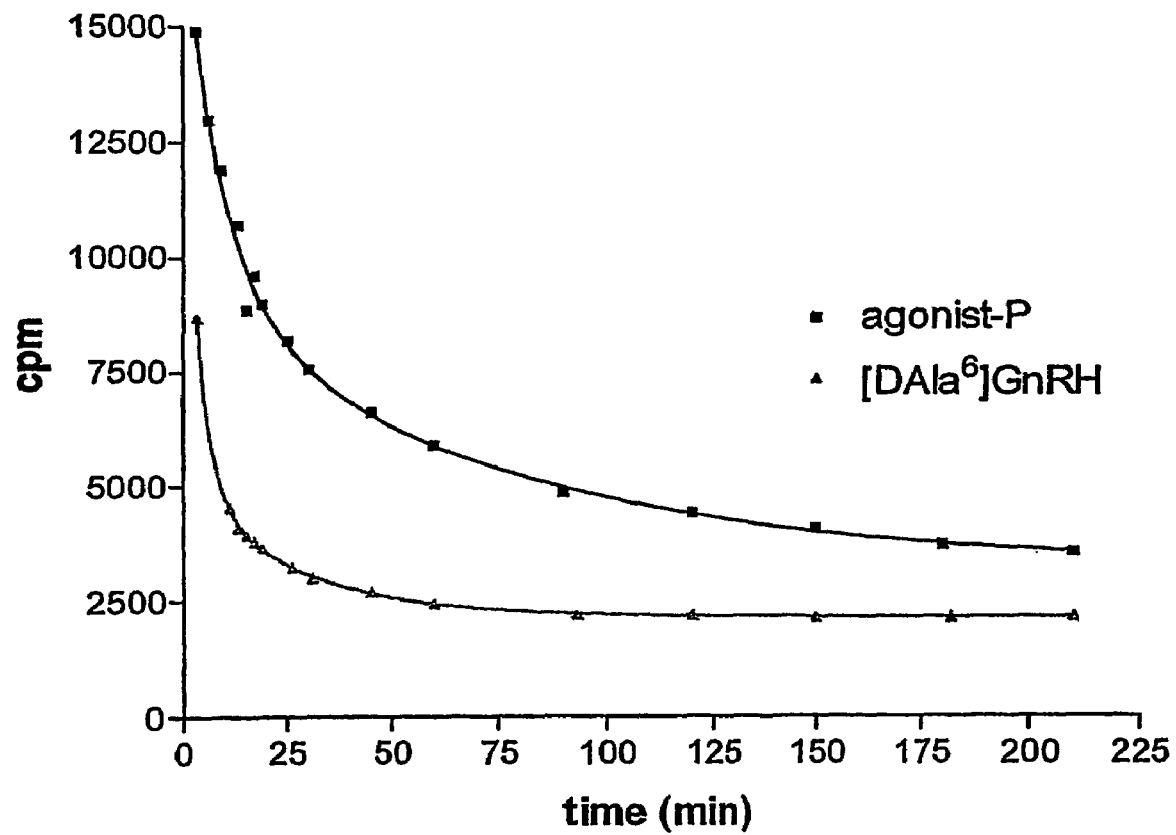
FIG. 6 shows the presence of radiolabelled GnRH agonist-progesterone (■) and [D-Ala$^6$]GnRH (▲) in the whole blood of two male rabbits injected intravenously into the ear vein with approximately 15,000,000 cpm of $^{125}$I-GnRH agonist-progesterone conjugate or $^{125}$I-D-Ala$^6$]GnRH in 500 μl saline. Disappearance from whole blood was measured over 3.5 hours.
Figure 7:
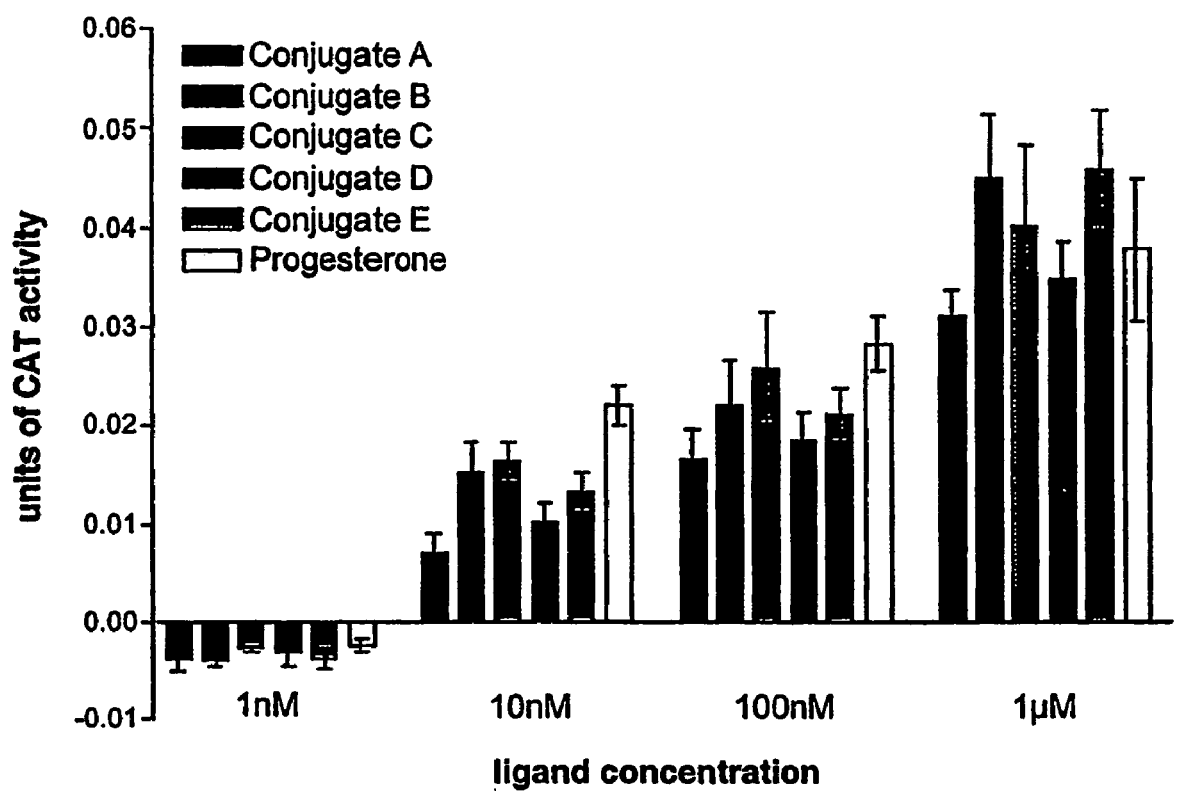
FIG. 7 shows the effect of conjugates A, B, C, D and E and progesterone on the activation of the CAT reported gene linked to the progesterone receptor in T47D cells as measured by CAT activity.

The in vivo male rabbit experiments were designed to investigate the half-life of iodinated GnRH agonist-progesterone in comparison to that of an unmodified GnRH agonist (FIG. 6). The disappearance of the iodinated compound was used to calculate both the half-life of the first phase corresponding to the distribution of the molecule and the second phase representing metabolism and renal clearance. The GnRH agonist-progesterone conjugate had a second phase half-life of 53±13 mins (n=3). The GnRH agonist [D-Ala$^6$] GnRH had a second phase half-life of 21±3 mins (n=2). The difference in half-life between the two analogues was not statistically significant (p>0.05, STT), but this may have reached significance with a greater number of samples.

Discussion

GnRH is suggested to adopt a horseshoe conformation when binding to the GnRH receptors[10], therefore the hormones were conjugated were to a D-Lys amino acid in the central position (6) or at position (7) or at the N-terminus, utilising the amine group of the side chain or N-terminus.

It was hoped that this would minimise any steric hindrance resulting from the addition of the steroid molecule. Indeed the right shift in the ED$_{50}$, determined by whole cell binding assay, for antagonist A versus antagonist A-progesterone was significant (p<0.01, STT), confirming a reduced affinity for the receptor. However this was not the case with the antagonist B versus antagonist B-progesterone, indicating that any steric hindrance was dependent on the peptide sequence. Analysis of the inositol phosphate second messenger system was included to identify whether the modification of the GnRH analogue had the potential to introduce a limited agonism at the GnRH receptor. This was not seen for either antagonist A-progesterone or antagonist B-progesterone. The ability to stimulate inositol phosphate production was also investigated for the GnRH agonist-progesterone conjugate. Again it was shown that no significant reduction in stimulation of this system occurred as a result of steroid conjugation. Thus it was concluded that the GnRH analogue-progesterone conjugates retained GnRHR binding and antagonism despite significant chemical modification.

The novel conjugated GnRH antagonists investigated here were shown to bind plasma proteins in in vitro assay and this is likely to be the case in vivo. This will result in an extended half-life of conjugated GnRH analogues, as seen in the experiments of half-life in rabbits. The prolonged exposure to the unbound conjugate, continuously released from binding proteins, will bind to the GnRHR as the free component is metabolised.

This study has proven that the GnRH analogue-steroid molecules can be completely bifunctional with respect to GnRH and progesterone receptor binding and activation. This is in contrast to the previous study by Rahimipour et al[22] where only the GnRH aspect of the emodic acid conjugates was functional. This also provides important information for conjugation of other molecules to steroids, identifying that chemical modification through C21 does not significantly alter the interaction between progesterone and its receptor.

The administration of steroid-conjugated and unconjugated GnRH antagonists to male marmosets has allowed analysis of duration of action without the additional fear of binding to CBG. Most new world primates share an apparent resistance to glucocorticoids, with elevated total cortisol and a reduction in the cortisol serum capacity[8]. The *Callithrix jacchus* was thus an in vivo model with little functional CBG capacity (confirmed by plasma protein binding assay, data not shown) to allow analysis of bioactivity without plasma protein interaction. Therefore the prolonged depression of testosterone production was in all probability due to the increased hydrophobicity of the molecule resulting in extended half-life due to hydrophobic interactions with plasma proteins, membranes and a depot effect in fat. Acknowledgement of this effect is vital to understanding the results seen in other primate models with CBG physiology similar to that of humans. This data is of value because of the similarity of the marmoset physiology to humans and the more complex pharmacology of GnRH antagonists.

The in vivo experiments carried out in the male rabbit, a species that produces CBG[17], demonstrated the increased half-life of a GnRH agonist-progesterone conjugate in comparison to a similar unconjugated agonist. The GnRH agonist used was hydrophilic in comparison to the hydrophobic sequences of the antagonists examined here. This implies that the increase in half-life was in all probability due to the conjugation to progesterone and hence binding to plasma transport proteins in the rabbit studies. Thus the conjugation of short peptide molecules such as GnRH and its analogues is a possible mechanism for enhancement of circulatory half-life.

In summary GnRH analogue-steroid hormone conjugates were designed to introduce plasma steroid binding protein capacity, thus modifying the pharmacokinetics and the pharmacodynamics of the GnRH analogues. A GnRH agonist pGlu-His-Trp-Ser-Tyr-D-Lys-Leu-Arg-Pro-GlyNH$_2$, and two antagonists of GnRH [AcD-Nal$^1$,D-Cpa$^2$,D-Pal$^3$,Arg$^5$,D-Lys$^6$,D-Ala$^{10}$]GnRH, and [Ac-ΔPro$^1$,D-Fpa$^2$,D-Trp$^3$,D-Lys$^6$] GnRH, designated antagonists A and B respectively, were conjugated through the D-Lysine side chain in position 6 of the decapeptide to a hemisuccinate linker at C11 or C21 of progesterone by dicyclohexylcarbodiimide (DCC). Products were purified by diode-array HPLC and identified by mass spectrometry. The GnRH agonist-progesterone and the GnRH antagonist-progesterone conjugates each bound to the pituitary type I human GnRH receptor in whole cell binding assay. Inhibition of GnRH-stimulated inositol phosphate production demonstrated all the agonist and antagonist conjugates were pure antagonists at the GnRH receptor. The three peptide-progesterone conjugates were shown to compete with [$^3$H]progesterone for plasma protein binding sites in pregnant Guinea Pig plasma. The IC$_{50}$ for antagonist peptide A-progesterone was 8.5±2.8×10$^{-7}$M (n=5), 4.5±0.8×10$^{-7}$M (n=3) for antagonist peptide B-progesterone and 2.9±1.2× 10$^{-10}$M (n=1) for the agonist-progesterone conjugate. In vivo bioactivity of antagonist-progesterone conjugates was demonstrated in male marmosets as a reduction in plasma testosterone concentrations after subcutaneous injection. Intravenous injection of GnRH agonist-progesterone into male rabbits showed the half-life of the antagonist was extended by the conjugation to a progesterone molecule.

In conclusion, specific novel GnRH hapten molecules made according to the invention have been designed, produced and investigated both in vitro and in vivo. The chemical modification of the GnRH analogues did not significantly affect in vitro activity and the half-life of the GnRH agonist-progesterone conjugate in the male rabbit has been extended. These and similar molecules overcome some of the problems associated with peptide pharmaceuticals. The conjugation of GnRH antagonists to carrier molecules or inclusion in a particle for uptake, in addition to steroid hormone will potentially enhance oral bioavailability and prolong duration of action.

EXAMPLE 2

Treatment of Breast Cancer with GnRH Conjugate Compound

A patient suffering from breast cancer is administered teverelix conjugated to 21-hydroxyprogesterone via a succinate linking group at a dosing quantity and frequency such that the therapeutic level of active agent at the site of treatment is maintained at a level ideally EC90 but preferably not less than EC50 throughout the treatment period. The treatment is delivered orally or more locally depending on patient acceptability, avoidance of side effects and systemic bioavailability.

EXAMPLE 3

Use of a GnRH Conjugate Compound as a Veterinary Contraceptive

A female horse is administered a GnRH antagonist conjugated to 21-hydroxyprogesterone via a succinate linking group at a dosing quantity and frequency so as to prevent conception. The treatment is delivered as a slow-release formulation which is administered by injection.

REFERENCES

1. Anderson R A (2000) Hormonal contraception in the male. *Br Med Bull* 56(3):717-728.
2. Christin-Maitre S, Olivennes F, Dubourdieu S, Chabbert-Buffet N, Charbonnel B, Frydman R, and Bouchard P (2000) Effect of gonadotropin-releasing hormone (GnRH) antagonist during the LH surge in normal women and during controlled ovarian hyperstimulation. *Clin Endocrinol (Oxf)* 52(6):721-726.
3. Danforth D R, Williams R F, Hsiu J G, Roh Sl, Hahn D., McGuire J L, Hodgen G D 1990 Intermittent GnRH antagonist plus progestin contraception conserving tonic ovarian estrogen secretion and reducing progestin exposure. *Contraception* 41(6):623-631.
4. Ditkoff E C, Cassidenti D L, Paulson R J, Sauer M V, Paul W L, Rivier J, Yen S S C, Lobo R A (1991) The gonadotropin-releasing hormone antagonist (Nal-Glu) acutely blocks the luteinizing hormone surge but allows for resumption of folliculogenesis in normal women. *Am J Obs Gyne* 165(6 Pt 1):1811-1817.
5. Fraser H M, Nestor J J Jr, Vickery B H (1987) Suppression of luteal function by a luteinizing hormone-releasing hormone antagonist during the early luteal phase in the stumptailed monkey and the effects of subsequent administration of human chorionic gonadotropin. *Endocrinol* 121(2):612-628.
6. Fraser H M, Lunn S F, Cowen G M, Smith K B, Conn P M, (1991) Effect of late follicular phase administration of antide on ovulation and inhibin secretion in macaques. *Contraception* 44(6):667-676.
7. Kenigsberg D, Hodgen G D, (1986) Ovulation inhibition by administration of weekly gonadotropin-releasing hormone antagonist. *J Clin Endocrinol Metab* 62(4): 734-738.
8. Klosterman L L, Murai J T, Siiteri P K (1986) Cortisol levels, binding, and properties of corticosteroid-binding globulin in the serum of primates. *Endocrinol* 118(1):424-434.
9. Mattox V R, Litwiller R D, Nelson A N (1979) A comparison of procedures for attaching steroidal glucosiduronic acids to bovine serum albumin. *J Steroid Biochem* 10:167-172.
10. Millar R P, Assefa D, Ott T, Pawson A, Troskie B, Wakefield L, Katz A GnRH and GnRH analogues: Structure, actions and clinical applications. *Horm Frontier Gynecol* 5(4):77-83.
11. Nestor J J, Tahilramani R, Ho T L, Goodpasture J C, Vickery B H, Ferrandon P (1992) Potent gonadotropin releasing hormone antagonists with low histamine-releasing activity. *J Med Chem* 35(21):3942-3948
12. Pavlou S N, Brewer K, Farley G, Lindner J, Bastias M, Rogers J, Swift L L, Rivier J E, Vale W W, Conn P M, Herbert C M (1991) Combined administration of a gonadotropin-releasing hormone antagonist and testosterone in men induces reversible azoopermia without loss of libido. *J Clin Endo Metab* 73(6):1360-1369.
13. Pavlou S N, Brewer K, Farley G, Lindner J, Bastias M, Rogers J, Swift L L, Rivier J E, Vale W W, Conn P M, Herbert C M (1991) Combined administration of a gonadotropin-releasing hormone antagonist and testosterone in men induces reversible azoopermia without loss of libido. *J Clin Endo Metab* 73(6):1360-1369.
14. Pavlou S N, Brewer K, Farley G, Lindner J, Bastias M, Rogers J, Swift L L, Rivier J E, Vale W W, Conn P M, Herbert C M (1991) Combined administration of a gonadotropin-releasing hormone antagonist and testosterone in men induces reversible azoopermia without loss of libido. *J Clin Endo Metab* 73(6):1360-1369.
15. Russell-Jones G J, Westwood S W, Farnworth P G, Findlay J K, Burger H G, (1995) Synthesis of LHRH antagonists suitable for oral administration via the Vitamin B12 uptake system. Bioconjugate Chem 6:34-42.
16. Siiteri P K, Murai J T, Hammond G L, Nisker J A, Raymoure W J, Kuhn R W (1982) The serum transport of steroid hormones *Rec Prog Horm Res* 38:457-510.
17. Seal U S, Doe R P (1965) Vertebrate distribution of Corticosteroid-binding globulin and some endocrine effects on concentration. *Steroids* 5:827-841.
18. Swerdloff R S, Bagatell C J, Wand C, Anawalt B D, Berman N, Steiner B, Bremner W J (1998) Suppression of spermatogenesis in man induced by Nal-Glu gonadotropin releasing hormone antagonist and testosterone enanthate (TE) is maintained by TE alone. *J Clin Endo Metab* 83(10): 3527-3533.
19. Westphal U (1993) Steroid-protein interaction: From past to present. *J Steroid Biochem* 19(1):1-15.
20. McEwan J F, Veitch H S, Russell-Jones G J (1999) Synthesis and Biological Activity of Ribose-5'-Carbamate Derivatives of Vitamin $B_{12}$. *Bioconjugate Chem.* 20, 10, 1131-1136.
21. Alsenz J, Russell-Jones G J, Westwood S, Levet-Trafit B, de Smidt P C (2000) Oral Absorption of Peptides Through the Cobalamin (Vitamin B12) Pathway in the Rat Intestine. *Pharmaceutical Research,* 21, Vol. 17, No. 7, 2000.
22. Rahimipour S, Ben-Aroya N, Fridkin M, Koch Y (2000) Design, Synthesis, and Evaluation of a Long-Acting, Potent Analogue of Gonadotropin-Releasing Hormone. *J. Med. Chem.* 22, 44, 3645-3652.
23. Thau (1984) Luteinizing hormone-releasing hormone (LHRH) and its analogs for contraception in women: a review. *Contraception,* 29(2): 143-162.
24. Millar R. P. (2003) Gonadatropin-releasing hormones and their receptors, Chapter 1, Reproductive Medicine: Molecular, Cellular and Genetic Fundamentals, Eds.

B.C.J.M. Fauser et al, The Parthenon Publishing Group, New York, USA. ISBN: 1-84214-019-1.

25. Millar R. P. et al (2000) Progress towards the development of non-peptide orallymactive gonadatropin-releasing hormone (GnRH) antagonists: therapeutic implications. *Br. Med. Bull.* 56(3): 761-772.

26. Burton & Westphal (1972) Steroid hormone-binding proteins in blood plasma. *Metabolism* 21(3): 253-276.

27. Cunningham G. R. et al (1981) Steroid structural requirements for high affinity binding to human sex steroid binding protein (SBP). *Steroids* 38(3): 243-262.

28. Mickelson K. E. et al (1981) Steroid-protein interactions. Human corticosteroid binding globulin: Some physiochemical properties and binding specificity. *Biochemistry* 20: 6211-6218.

The invention claimed is:

1. A compound comprising a gonadotrophin releasing hormone (GnRH) analogue conjugated to a steroid hormone or a progesterone derivative which is able to bind to a plasma hormone binding protein, wherein the steroid hormone is estradiol, progesterone, cortisol, corticosterone, estrone, testosterone or dihydroxytestosterone, and wherein the progesterone derivative is 11α-hydroxyprogesterone or 21-hydroxyprogesterone.

2. A compound according to claim 1 wherein the GnRH analogue is a peptide analogue.

3. A compound according to claim 2 wherein the GnRH analogue is a nonapeptide or a decapeptide.

4. A compound according to claim 1 wherein one of the amino acid residues of the GnRH analogue is a D-amino acid.

5. A compound according to claim 4 wherein the D-amino acid is D-Lys.

6. A compound according to claim 4 wherein the D-amino acid is at position 6.

7. A compound according to claim 1 wherein the GnRH analogue is a GnRH antagonist.

8. A compound according to claim 7 wherein the GnRH antagonist is [AcD-Nal[1], D-Cpa[2], D-Pal[3], Arg[5], D-Lys[6], D-Ala[10]]GnRH, or [Ac-ΔPro[1], D-Fpa[2], D-Trp[3], D-Lys[6]] GnRH.

9. A compound according to claim 7 wherein the GnRH antagonist is Cetrorelix, Ganirelix, Abarelix, Antide, Teverelix, FE200486, Nal-Glu, A-75 998, A-76154, A-84861, D-26344, D-63153, ramorelix, degarelix, NBI-42902, Org-30850, detirelix, iturelix, TAK-013, TAK810, AN 207, AcD-Nal-D-Cpa-D-Pal-Ser-Arg-D-Lys-Leu-Arg-Pro-D-Ala-NH$_2$; Ac-ΔPro-D-Fpa-D-Trp-Ser-Tyr-D-Lys-Leu-Arg-Pro-Gly-NH$_2$; AcD-Nal-D-Cpa-D-Pal-Ser-Arg-D-Lys-Lys-Leu-Arg-D-Ala-NH$_2$; D-Pal-Ser-Arg-D-Lys-Leu-Arg-Pro-D-Ala-NH$_2$; AcD-Nal-D-Cpa-D-Pal-Ser-Arg-D-Lys-Lys-Arg-Pro-D-Ala-NH$_2$; [D-Pyr[1], D-Phe[2], D-Trp[3-6]]GnRH; D-Lys[6]Antide; Lys[5] Antide or Lys[8] Antide.

10. A compound according to claim 1 wherein the GnRH analogue is a GnRH agonist.

11. A compound according to claim 10 wherein the GnRH agonist is pGlu-His-Trp-Ser-Tyr-D-lys-Leu-Arg-Pro-GlyNH$_2$, Lupron, Zoladex, Supprelin, Synarel, Buserelin, leuprolide, goserelin, deslorelin, ProMaxx-100, avorelin, histrelin, nafarelin, leuprorelin or triptorelin.

12. A compound according to claim 1 wherein the compound retains the in vivo hormonal activity of the steroid hormone or progesterone derivative.

13. A compound according to claim 1 wherein the compound has no in vivo hormonal activity of the steroid hormone or progesterone derivative.

14. A compound according to claim 1 wherein the steroid hormone or progesterone derivative binds to a plasma hormone binding protein in vivo.

15. A compound according to claim 1 wherein the hormone binding protein is a globulin.

16. A compound according to claim 15 wherein the plasma hormone binding protein is cortisol binding globulin (CBG), sex hormone binding globulin (SHBG), or progesterone binding globulin (PBG) or albumin.

17. A compound according to claim 1 wherein the conjugated GnRH analogue and the steroid hormone or progesterone derivative are cleavable.

18. A compound according to claim 1 wherein the GnRH analogue and the steroid hormone or progesterone derivative are directly conjugated.

19. A compound according to claim 1 wherein the GnRH analogue and the steroid hormone or progesterone derivative are conjugated via a linking group.

20. A compound according to claim 19 wherein the linking group comprises a succinate linker or a derivative thereof.

21. A compound according to claim 1 wherein the GnRH analogue has a D-lysine residue, and the GnRH analogue is conjugated to the steroid hormone or progesterone derivative via the D-lysine.

22. A compound according to claim 1 which has a longer half-life in vivo than native GnRH.

23. A compound according to claim 1 which has a longer duration of activity in vivo than native GnRH.

24. A compound according to claim 1 having the formula

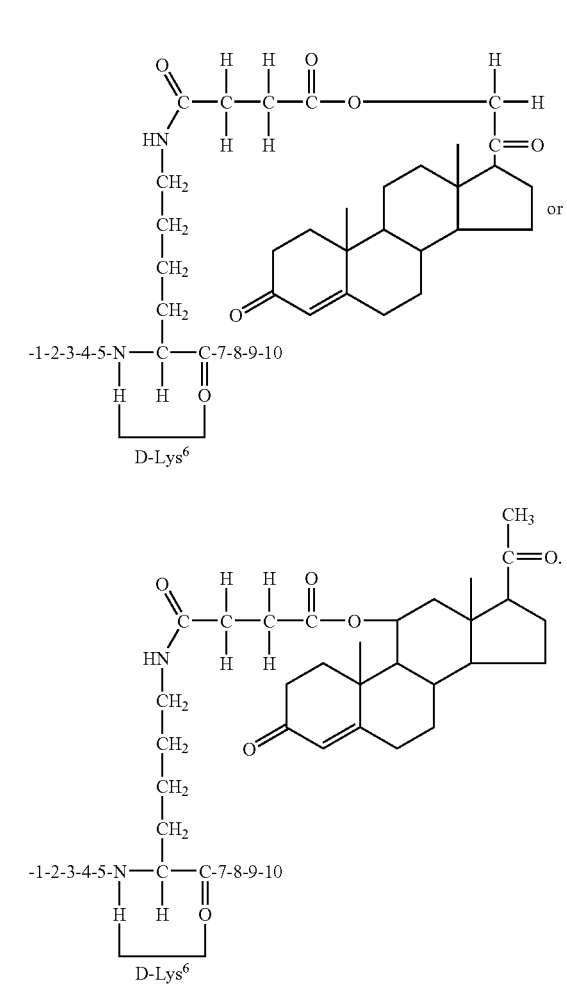

25. A compound according to claim 1 which is: AcD-Nal-D-Cpa-D-Pal-Ser-Arg-D-Lys-Leu-Arg-Pro-D-Ala-NH$_2$ conjugated to 21-hydroxyprogesterone 21-succinate at the ε amine of D-Lys at position 6; Ac-ΔPro-D-Fpa-D-Trp-Ser-Tyr-D-Lys-Leu-Arg-Pro-Gly-NH$_2$ conjugated to 21-hydroxyprogesterone 21-succinate at the ε amine of D-Lys at position 6; AcD-Nal-D-Cpa-D-Pal-Ser-Arg-D-Lys-Lys-Leu-Arg-D-Ala-NH$_2$ conjugated to 21-hydroxyprogesterone 21-succinate at the ε amine of Lys at position 7; D-Pal-Ser-Arg-D-Lys-Leu-Arg-Pro-D-Ala-NH$_2$ conjugated to 21-hydroxyprogesterone 21-succinate at the N-terminal amine of D-Pal; AcD-Nal-D-Cpa-D-Pal-Ser-Arg-D-Lys-Lys-Arg-Pro-D-Ala-NH$_2$ conjugated to 21-hydroxyprogesterone 21-succinate at the ε amine of Lys at position 7; or [DLys$^6$] GnRH conjugated to 11α-hydroxyprogesterone 11-succinate at the ε amine group of the D-Lys at position 6.

26. A compound according to claim 1 which is bound to a plasma hormone binding protein.

27. A compound according to claim 26 wherein the plasma hormone binding protein is CBG, SHBG, or albumin.

28. A pharmaceutical composition comprising a compound according to claim 1 and a pharmaceutically acceptable excipient, carrier or diluent.

29. A pharmaceutical composition according to claim 28 which is suitable for oral administration.

30. A pharmaceutical composition according to claim 28 which is a slow-release formulation.

31. A method of reducing the fertility of an individual comprising administering a compound according to claim 1 to the individual.

32. A method of treating a hormone-dependent disease or condition comprising administering a compound according to claim 1 to an individual in need thereof.

33. A method according to claim 32 wherein the hormone-dependent disease or condition is selected from a hormone-dependent cancer, benign prostatic hypertrophy, endometriosis, uterine fibroids, premenstrual syndrome, polycystic ovarian syndrome, hirsutism, acne vulgaris, precocious puberty, acute intermittent porphyria, cryptoorchidism and delayed puberty.

34. A method according to claim 33 wherein the hormone-dependent cancer is breast cancer, prostate cancer, uterine cancer or endometrial cancer.

35. A method of treating infertility comprising administering a compound according to claim 1 to an individual in need thereof.

36. A method of modulating the production of gonadotrophins or sex hormones in vivo comprising administering a compound according to claim 1 to an individual.

37. A method of modifying a GnRH analogue so that it has an increased in vivo half-life compared to GnRH, the method comprising conjugating the GnRH analogue to a steroid hormone or progesterone derivative which is able to bind to a plasma hormone binding protein, wherein the steroid hormone is estradiol, progesterone, cortisol, corticosterone, estrone, testosterone or dihydroxytestosterone, and wherein the progesterone derivative is 11α-hydroxyprogesterone or 21-hydroxyprogesterone.

38. A method of modifying a GnRH analogue so that it has an increased duration of activity in vivo compared to GnRH, the method comprising conjugating the GnRH analogue to a steroid hormone or progesterone derivative which is able to bind to a plasma hormone binding protein, wherein the steroid hormone is estradiol, progesterone, cortisol, corticosterone, estrone, testosterone or dihydroxytestosterone, and wherein the progesterone derivative is 11α-hydroxyprogesterone or 21-hydroxyprogesterone.

39. A method according to claim 37 wherein the conjugating step comprises conjugating the GnRH analogue and the steroid hormone or progesterone derivative via a linking group.

40. A method according to claim 37 further comprising binding the steroid hormone or progesterone derivative to a plasma hormone binding protein.

41. A method according to claim 40 wherein the plasma hormone binding protein is CBG, SHBG, or albumin.

42. A method according to claim 37 further comprising determining the in vivo half-life of the conjugated GnRH analogue.

43. A method according to claim 42 further comprising comparing the in vivo half-life of the conjugated GnRH analogue with the in vivo half-life of GnRH to identify a GnRH analogue having an increased in viva half-life compared to GnRH.

44. A method according to claim 31 wherein the compound is present in a pharmaceutical composition that comprises a pharmaceutically acceptable excipient, carrier or diluent.

45. A method according to claim 32 wherein the compound is present in a pharmaceutical composition that comprises a pharmaceutically acceptable excipient, carrier or diluent.

46. A method according to claim 35 wherein the compound is present in a pharmaceutical composition that comprises a pharmaceutically acceptable excipient, carrier or diluent.

47. A method according to claim 36 wherein the compound is present in a pharmaceutical composition that comprises a pharmaceutically acceptable excipient, carrier or diluent.

48. A method according to claim 38 wherein the conjugating step comprises conjugating the GnRH analogue and the steroid hormone or progesterone derivative via a linking group.

49. A method according to claim 48 further comprising binding the steroid hormone or progesterone derivative to a plasma hormone binding protein.

50. A method according to claim 49 wherein the plasma hormone binding protein is CBG, SHBG, or albumin.

51. A method according to claim 38 further comprising determining the in vivo duration of activity of the conjugated GnRH analogue.

52. A method according to claim 51 further comprising comparing the in vivo duration of activity of the conjugated GnRH analogue with the in vivo duration of activity of GnRH to identify a GnRH analogue having an increased in vivo duration of activity compared to GnRH.

* * * * *